US008001971B2

(12) United States Patent
Boucher et al.

(10) Patent No.: US 8,001,971 B2
(45) Date of Patent: Aug. 23, 2011

(54) DEVICES, SYSTEMS, AND METHODS FOR STABILIZATION OR FIXATION OF MAGNETIC FORCE DEVICES USED IN OR ON A BODY

(75) Inventors: Ryan P. Boucher, San Francisco, CA (US); Joe Paraschac, San Jose, CA (US); Eric N. Doelling, Sunnyvale, CA (US); Edward M. Gillis, San Jose, CA (US); David H. Cole, Foster City, CA (US); Lionel M. Nelson, Los Altos, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1273 days.

(21) Appl. No.: 11/603,753

(22) Filed: Nov. 22, 2006

(65) Prior Publication Data

US 2007/0193587 A1    Aug. 23, 2007

Related U.S. Application Data

(63) Continuation-in-part of application No. 11/397,744, filed on Apr. 4, 2006, now Pat. No. 7,721,740, which is a continuation-in-part of application No. 10/806,372, filed on Mar. 22, 2004, now Pat. No. 7,441,559, which is a continuation-in-part of application No. 10/718,254, filed on Nov. 20, 2003, now Pat. No. 7,360,542, which is a continuation-in-part of application No. 10/656,861, filed on Sep. 6, 2003, now Pat. No. 7,188,627, which is a continuation-in-part of application No. 10/236,455, filed on Sep. 6, 2002, now Pat. No. 7,216,648.

(60) Provisional application No. 60/739,519, filed on Nov. 23, 2005, provisional application No. 60/441,639, filed on Jan. 22, 2003, provisional application No. 60/456,164, filed on Mar. 20, 2003, provisional application No. 60/754,839, filed on Dec. 29, 2005.

(51) Int. Cl.
*A61F 5/56* (2006.01)
(52) U.S. Cl. ........................................ 128/848; 128/860
(58) Field of Classification Search .................. 602/902; 128/846, 848, 859–862; 433/6
See application file for complete search history.

(56) References Cited

U.S. PATENT DOCUMENTS

| | | |
|---|---|---|
| 4,304,227 A | 12/1981 | Samelson |
| 4,978,323 A | 12/1990 | Freedman |
| 5,019,372 A | 5/1991 | Folkman et al. |
| 5,176,618 A | 1/1993 | Freedman |
| 5,220,918 A | 6/1993 | Heide et al. |
| 5,373,859 A | 12/1994 | Forney |
| 5,465,734 A | 11/1995 | Alvarez et al. |
| 5,649,540 A | 7/1997 | Alvarez et al. |
| 5,792,067 A | 8/1998 | Karell |
| RE36,120 E | 3/1999 | Karell |
| 5,979,456 A | 11/1999 | Magovern |
| 5,988,171 A | 11/1999 | Sohn et al. |

(Continued)

FOREIGN PATENT DOCUMENTS

DE    4307262    3/1993

*Primary Examiner* — Michael A. Brown

(57) ABSTRACT

Systems and methods prevent magnetic implant migration and extrusion in the upper airway. The systems and methods relate both to surgical techniques as well as structural features to address the problem of magnetic implant migration.

19 Claims, 23 Drawing Sheets

U.S. PATENT DOCUMENTS

| | | |
|---|---|---|
| 6,231,496 B1 | 5/2001 | Wilk et al. |
| 6,244,865 B1 | 6/2001 | Nelson et al. |
| 6,250,307 B1 | 6/2001 | Conrad et al. |
| 6,390,096 B1 | 5/2002 | Conrad et al. |
| 6,401,717 B1 | 6/2002 | Conrad et al. |
| 6,408,851 B1 | 6/2002 | Karell |
| 6,415,796 B1 | 7/2002 | Conrad et al. |
| 6,450,169 B1 | 9/2002 | Conrad et al. |
| 6,490,885 B1 | 12/2002 | Wilkinson |
| 6,523,541 B2 | 2/2003 | Knudson et al. |
| 6,523,542 B2 | 2/2003 | Knudson et al. |
| 6,636,767 B1 | 10/2003 | Knudson et al. |
| 6,742,524 B2 | 6/2004 | Knudson et al. |
| 6,955,172 B2 | 10/2005 | Nelson et al. |
| 7,073,505 B2 | 7/2006 | Nelson et al. |
| 7,077,143 B2 | 7/2006 | Knudson et al. |
| 7,077,144 B2 | 7/2006 | Knudson et al. |
| 7,188,627 B2 | 3/2007 | Nelson et al. |
| 2001/0047805 A1 | 12/2001 | Scarberry et al. |
| 2002/0066702 A1 | 6/2002 | Liu |
| 2004/0112390 A1* | 6/2004 | Brooks et al. ............... 128/863 |
| 2004/0249453 A1 | 12/2004 | Cartledge et al. |
| 2005/0004417 A1 | 1/2005 | Nelson et al. |
| 2005/0092332 A1 | 5/2005 | Conrad et al. |
| 2005/0159637 A9* | 7/2005 | Nelson et al. ............... 600/12 |

* cited by examiner

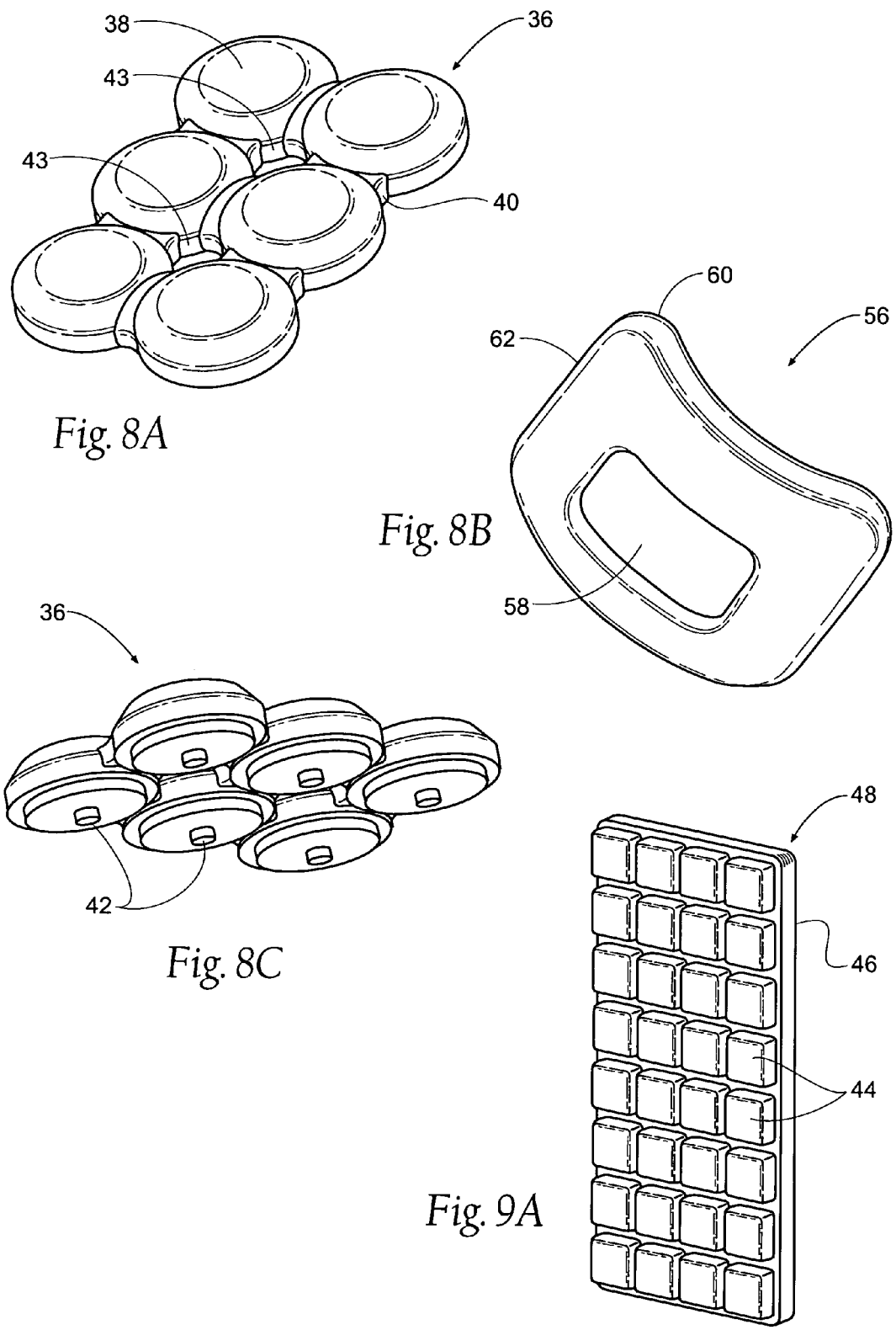

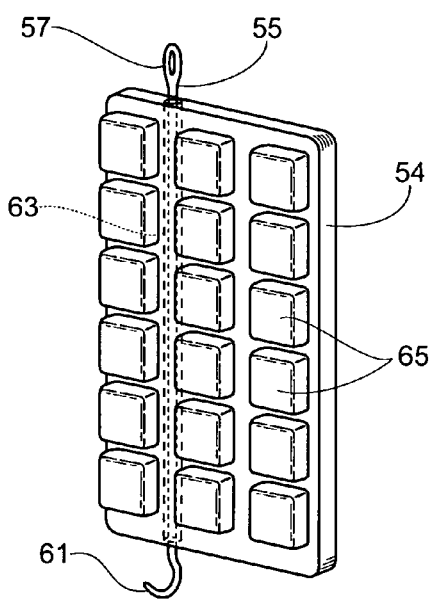
Fig. 11A (1)
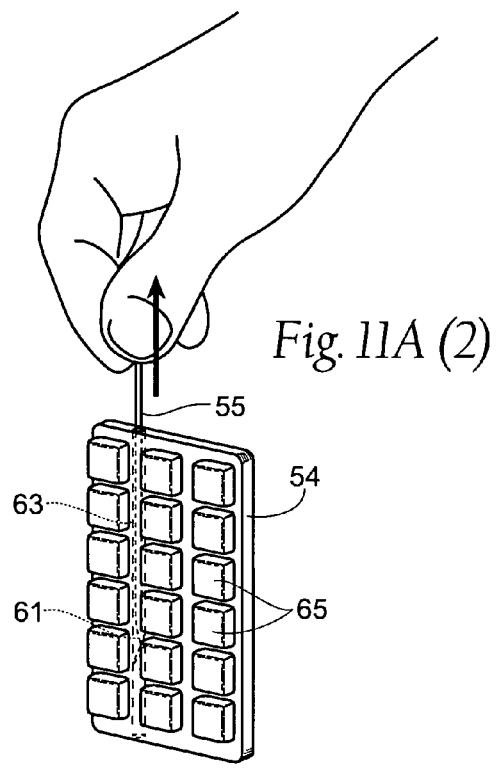
Fig. 11A (2)
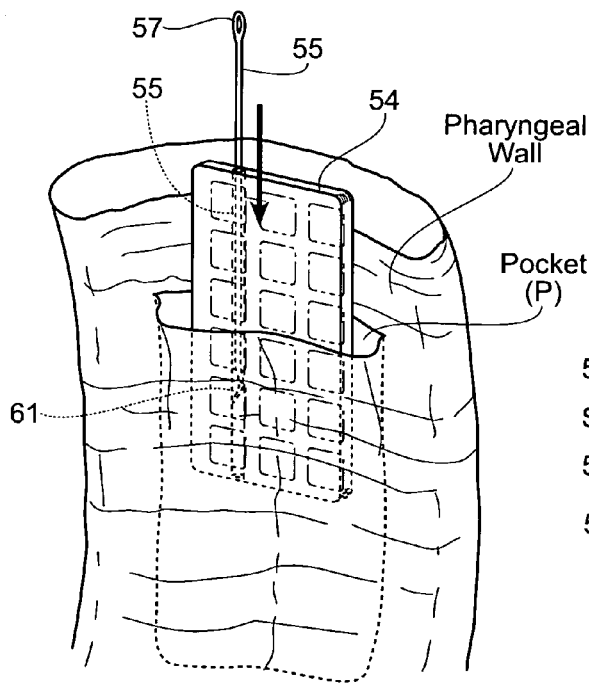
Fig. 11A (3)
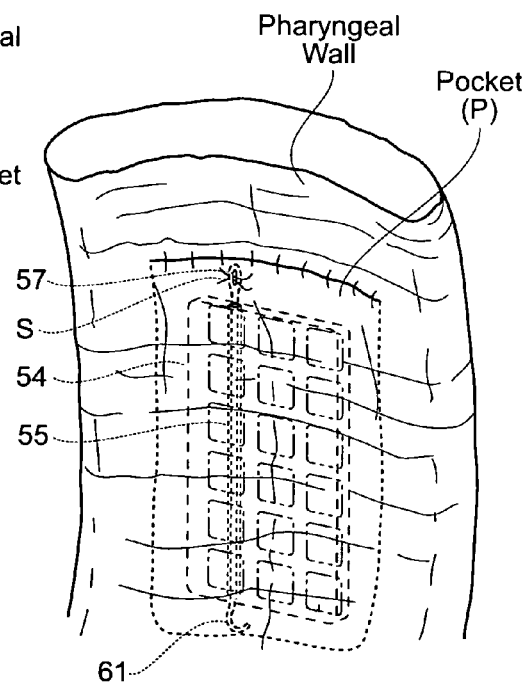
Fig. 11A (4)

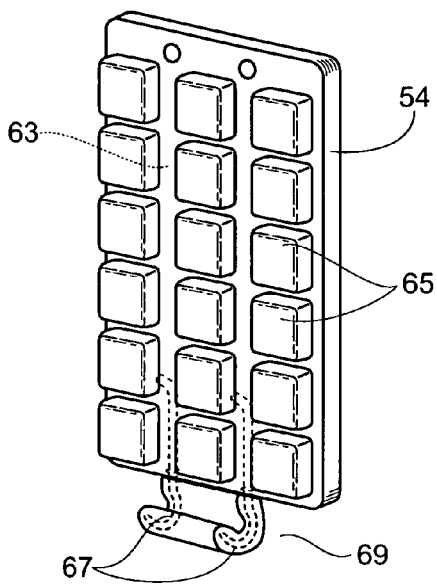
Fig. 11B (1)
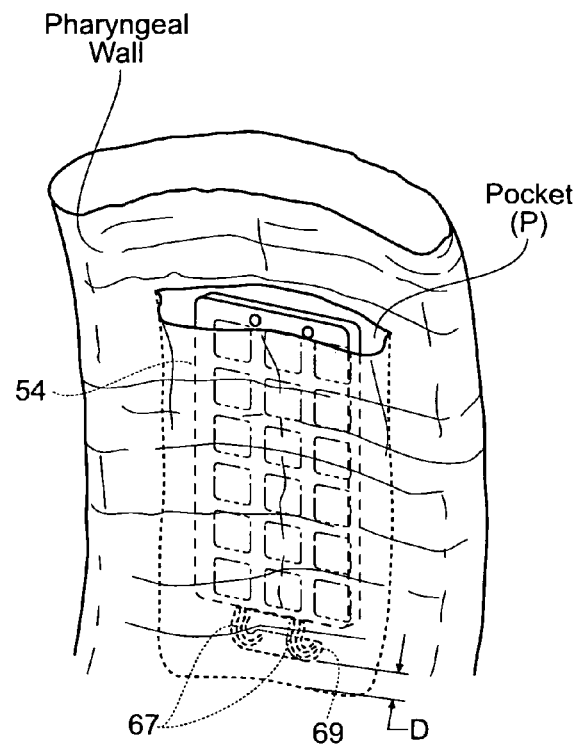
Fig. 11B (2)
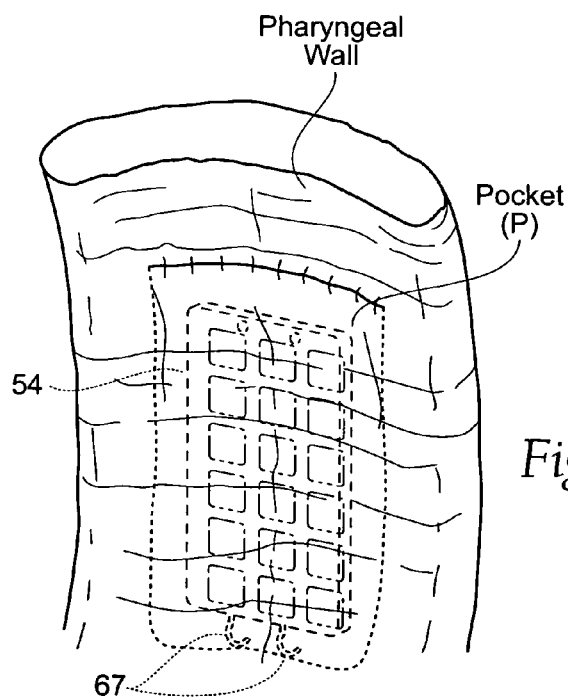
Fig. 11B (3)

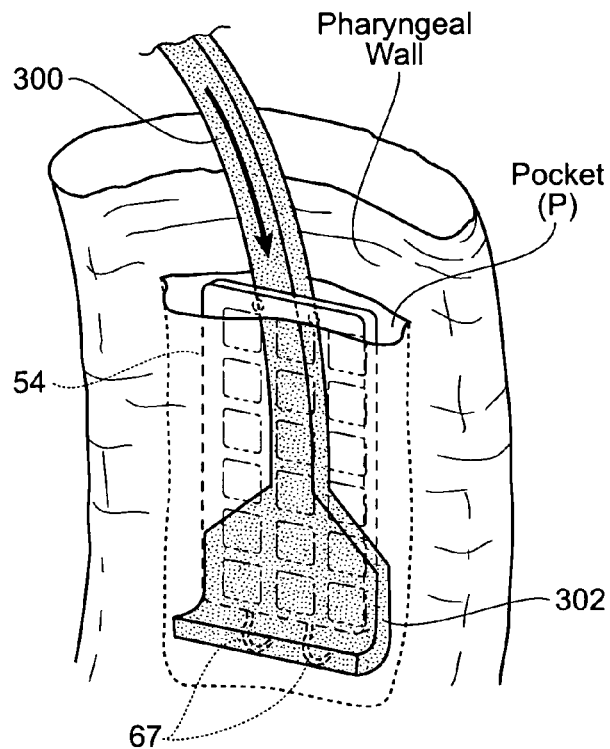
Fig. 11B (4)
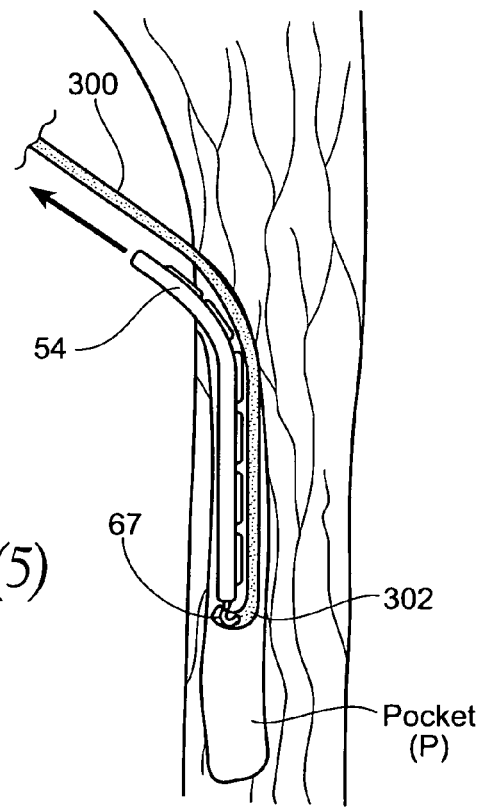
Fig. 11B (5)

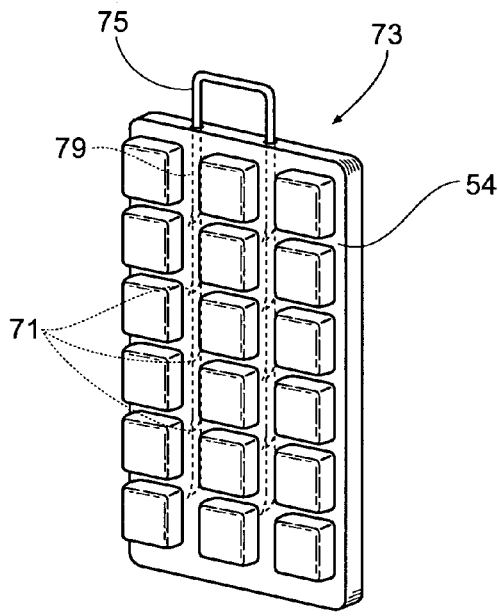
Fig. 11C (1)
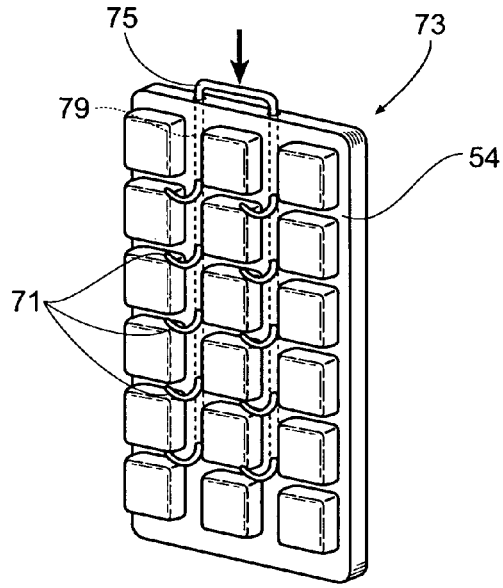
Fig. 11C (2)
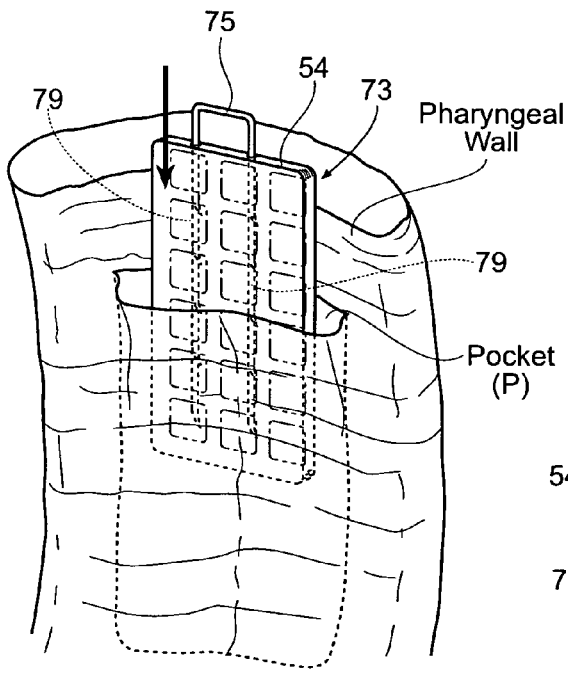
Fig. 11C (3)
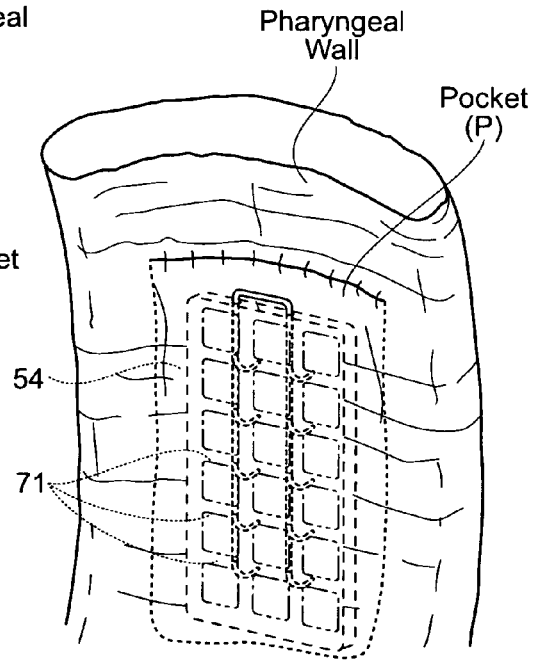
Fig. 11C (4)

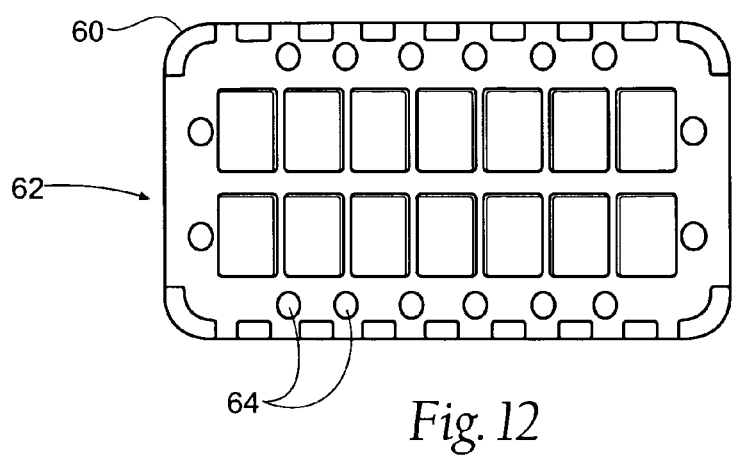
Fig. 12
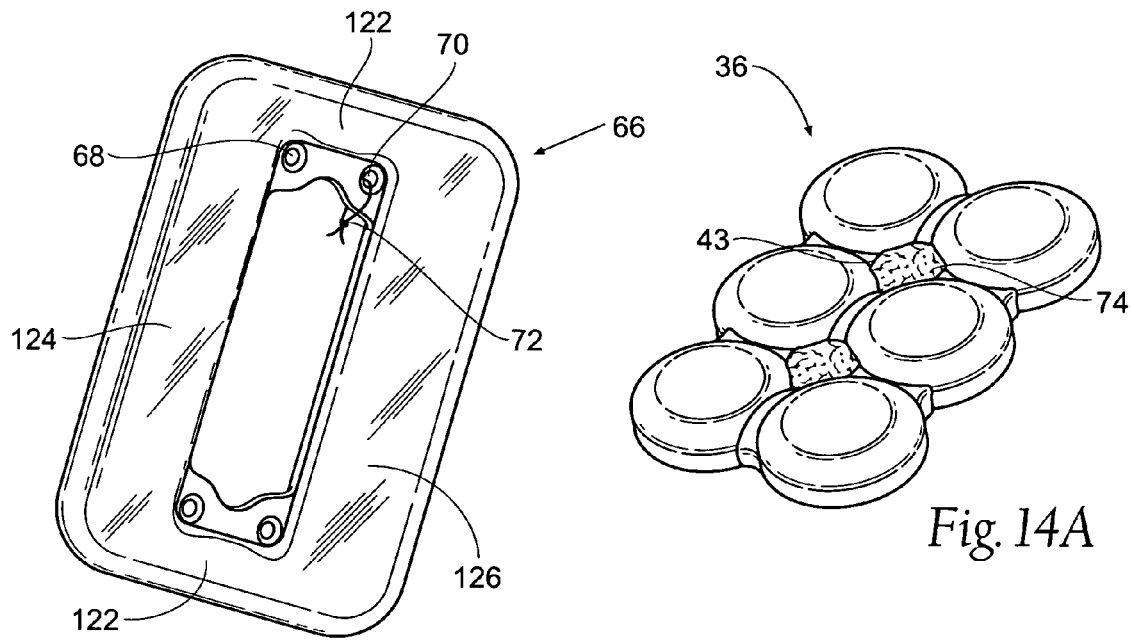
Fig. 13
Fig. 14A
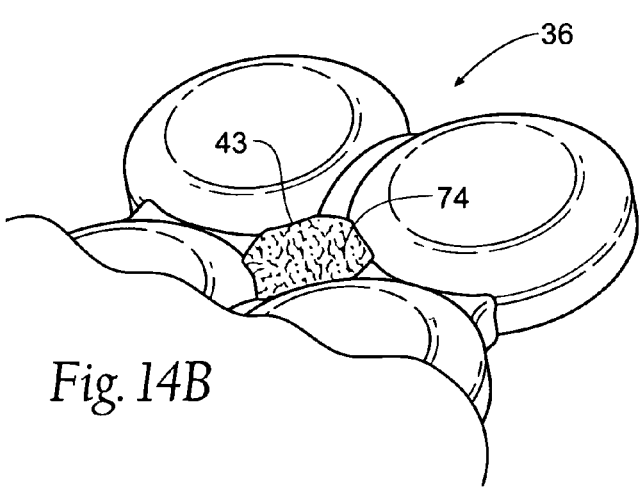
Fig. 14B

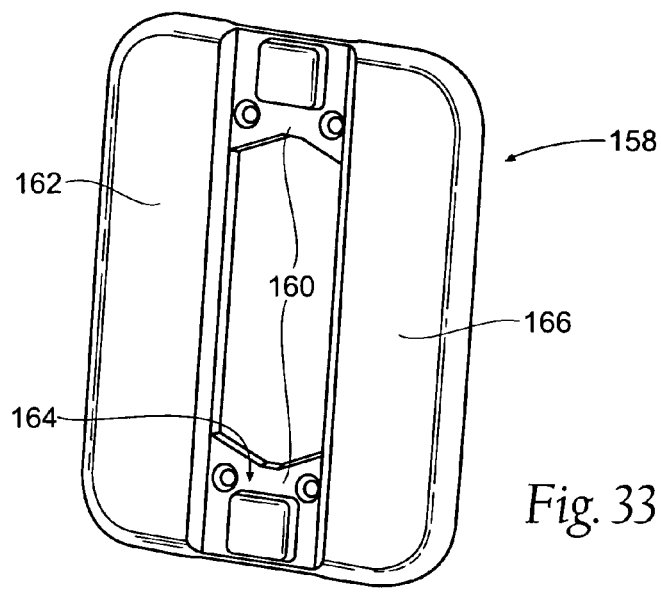
Fig. 33
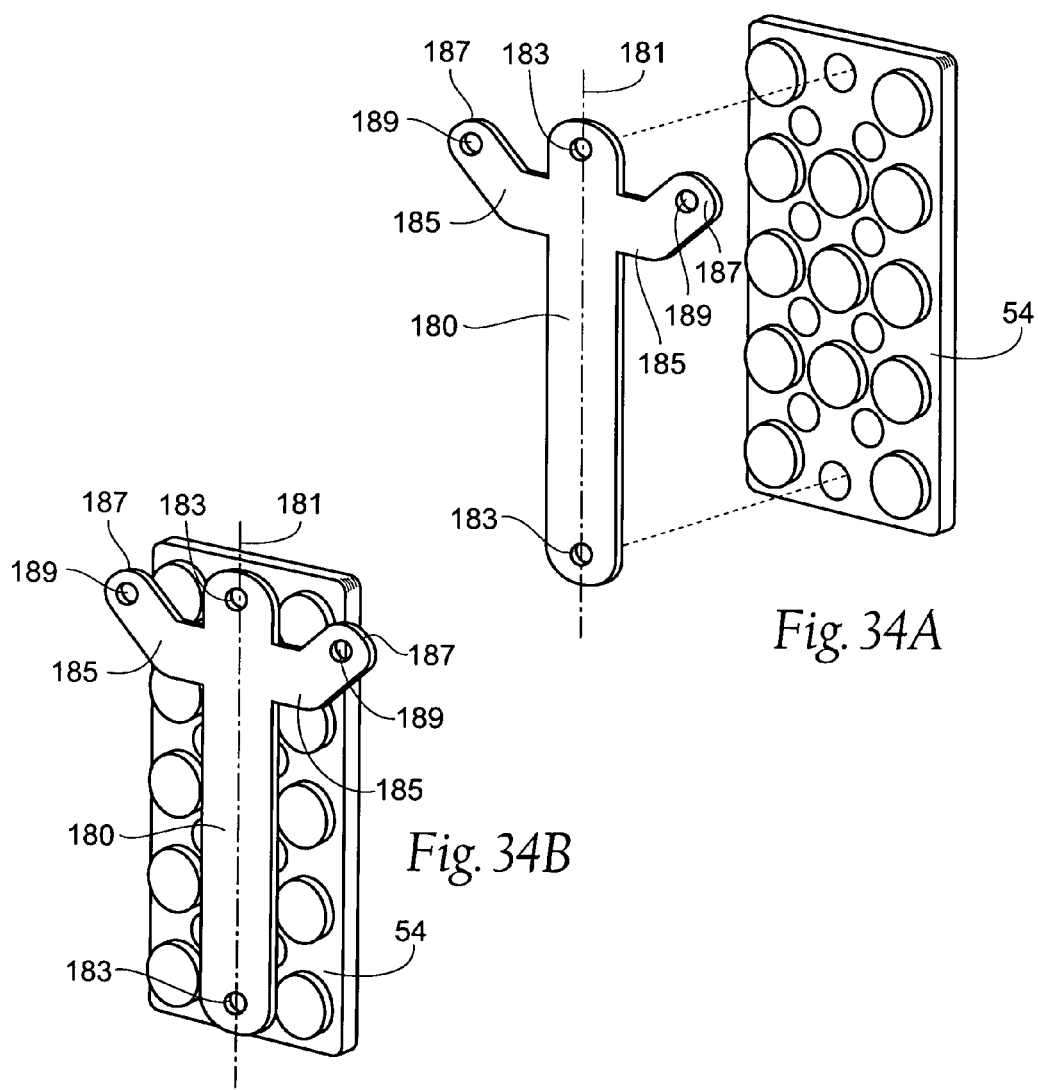
Fig. 34A
Fig. 34B

DEVICES, SYSTEMS, AND METHODS FOR STABILIZATION OR FIXATION OF MAGNETIC FORCE DEVICES USED IN OR ON A BODY

RELATED APPLICATIONS

This application claims the benefits of U.S. Provisional Patent Application Ser. No. 60/739,519, filed Nov. 23, 2005. This application is also a continuation-in-part of U.S. patent application Ser. No. 11/397,744 now U.S. Pat. No. 7,721,740, filed Apr. 4, 2006 entitled "Devices, Systems, and Methods Using Magnetic Force Systems In or On Tissue," which is a continuation-in-part of U.S. patent application Ser. No. 10/806,372, filed Mar. 22, 2004 now U.S. Pat. No. 7,441,559 entitled "Devices, Systems, and Methods to Fixate Tissue Within the Regions of the Body, Such as the Pharyngeal Conduit," which is a continuation-in-part of U.S. patent application Ser. No. 10/718,254, filed Nov. 20, 2003 now U.S. Pat. No. 7,360,542 entitled "Devices, Systems, and Methods to Fixate Tissue Within the Regions of the Body, Such as the Pharyngeal Conduit," which is a continuation-in-part of U.S. patent application Ser. No. 10/656,861, filed Sep. 6, 2003 now U.S. Pat. No. 7,188,627 entitled "Magnetic Force Devices, Systems, and Methods for Resisting Tissue Collapse within the Pharyngeal Conduit," which further claims the benefit of U.S. Provisional Patent Application Ser. No. 60/441,639, filed Jan. 22, 2003 and U.S. Provisional Patent Application Ser. No. 60/456,164, filed Mar. 20, 2003, and which is a continuation-in-part of U.S. patent application Ser. No. 10,236,455, filed Sep. 6, 2002 now U.S. Pat No. 7,216,648 and entitled "System and Method for Moving and/or Restraining Tissue in the Upper Respiratory System." This application also claims the benefit of U.S. Provisional Patent Application Ser. No. 60/754,839, filed Dec. 29, 2005. All of the foregoing are incorporated herein by reference.

FIELD OF THE INVENTION

The invention is directed to devices, systems, and methods for improved stabilization of magnetic force devices used in and/or on a body. The improved stabilization may be realized both during placement and at an implanted position.

BACKGROUND OF THE INVENTION

I. Characteristics of Sleep Apnea

First described in 1965, sleep apnea is a breathing disorder characterized by brief interruptions (10 seconds or more) of breathing during sleep. Sleep apnea is a common but serious, potentially life-threatening condition, affecting as many as 18 million Americans.

There are two types of sleep apnea: central and obstructive. Central sleep apnea, which is relatively rare, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. Normally, the muscles of the upper part of the throat keep the airway open to permit air flow into the lungs. When the muscles of the soft palate at the base of the tongue and the uvula (the small fleshy tissue hanging from the center of the back of the throat) relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" may be as high as 20 to 30 or more per hour. These breathing pauses are almost always accompanied by snoring between apnea episodes, although not everyone who snores has the condition. Sleep apnea can also be characterized by choking sensations.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all persons and mammals, the frequency of blockages will determine the seriousness of the disease and opportunity for health damage. When the incidence of blockage is frequent, corrective action should be taken.

II. Sleep and the Anatomy of the Upper Airway

The upper airway consists of a conduit that begins at the nasal valve, situated in the tip of the nose, and extends to the larynx. Although all tissue along this conduit is dynamic and responsive to the respiratory cycle, only the pharynx (the portion that starts behind the nasal cavity and ends in its connections to the supraglottic larynx is totally collapsible.

The cross sectional area of the upper airway varies with the phases of the respiratory cycle. At the initiation of inspiration (phase I), the airway begins to dilate and then to remain relatively constant through the remainder of inspiration (Phase II). At the onset of expiration (Phase III) the airway begins to enlarge, reaching maximum diameter and then diminishing is size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration. [ref: Schwab R J, Goldberg A N. Upper airway assessment: radiographic and other imaging techniques. Otolaryngol Clin North Am 1998; 31:931-968]

Sleep is characterized by a reduction in upper airway dilator muscle activity. For the individual with obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx [ref: Isono S. Remmers J, Tanaka A Sho Y, Sato J, Nishino T. Anatomy of pharynx in patients with obstructive sleep apnea and in normal subjects. J Appl Physiol 1997:82:1319-1326.] Although this phenomenon is often accentuated at specific sites, such as the velopharyngeal level [Isono], studies of closing pressures [Isono] supports dynamic fast MRI imaging that shows narrowing and collapse usually occurs along the entire length of the pharynx. [ref: Shellock F G, Schatz C J, Julien P, Silverman J M, Steinberg F, Foo T K F, Hopp M L, Westbrook P R. Occlusion and narrowing of the pharyngeal airway in obstructive sleep apnea: evaluation by ultrafast spoiled GRASS M R imaging. Am J of Roentgenology 1992:158:1019-1024.].

III. Treatment Options

To date, the only modality that addresses collapse along the entire upper airway is mechanical positive pressure breathing devices, such as continuous positive airway pressure (CPAP) machines. All other modalities, such as various surgical procedures and oral appliances, by their nature, address specific sectors of the airway (such as palate, tongue base and hyoid levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment in 6 months.

An alternative method would "splint" the airway during sleep that would give the benefits afforded by CPAP without some of its shortcomings would therefore be advantageous. In this method magnetic energy is used either attractively (opposite poles of two or more magnets facing one another, resulting in attractive forces) or repulsively (like poles of two or more magnets facing one another, resulting in forces which repel one another). Magnets implanted in the tongue interact either by attractive or repulsive forces with other magnets implanted in various organs of the upper airway system or external to the body within a neck collar.

Since the "splint" method using magnetic forces did not eliminate all magnetic interaction, implants within the tongue and pharyngeal wall often were often difficult to stabilize in their specified locations. The magnetic implants could interact with one another causing the implants to fold or lose their shape, as well as with magnetic instruments. The implants could also rotate or migrate from their original implant position.

The need remains for simple, cost-effective devices, systems, and methods for improved stabilization of magnetic force devices used in and/or on a body, including improved stabilization during placement and at an implanted position.

SUMMARY OF THE INVENTION

The invention provides devices, and methods to improve implant tolerance generally, prevent implant migration, and stabilize a magnetic implant in tissue, e.g., the tongue, oropharynx, and pharyngeal wall. The invention is particularly useful to prevent sleep disordered diseases such as Obstructive Sleep Apnea (OSA) and hypopnea (a partial obstruction of the airway during sleep).

One aspect of the invention provides an implant device comprising at least two ferromagnetic components carried by a support structure in a spaced apart relationship. The implant device includes at least one opening formed in the support structure between the ferromagnetic components. The openings can provide stabilization after implantation, e.g., by providing flexibility, and/or tissue in-growth, or placement of external fixation elements, such as a suture, or a staple, or glue.

In one embodiment, the support structure comprises a net-like array of openings.

In one embodiment, the opening occupies a geometric center of the support structure.

In one embodiment, the support structure is either generally U-shaped or O-shaped.

Another aspect of the invention provides an implant device comprising a ferromagnetic component carried on a a support structure. According to this aspect of the invention, at least one protrusion extends from the support structure. The protrusion is sized and configured for engaging tissue to stabilize the support structure. The protrusion can comprise, e.g., a barb, or a hook. In one embodiment, the implant device includes means for selectively withdrawing and extending the protrusion relative to the support structure.

Another aspect of the invention provides an implant device comprising a ferromagnetic component carried by a support structure. According to this aspect of the invention, the support structure includes a first side having a textured surface sized and configured for contact with tissue and a second side having a generally smooth surface. Contact between the textured first side and tissue within an airway stabilizes the implant, while the generally smooth surface, which faces the airway, minimizes interference with normal functions such as swallowing or speech.

Another aspect of the invention provides an implant device comprising a ferromagnetic component carried on a support structure. According to this aspect of the invention, the implant is shaped to prevent motion, migration and extrusion while implanted in tissue. The support structure can be sized and configured, e.g., with rounded corners, and/or irregular outer edges forming alternating wide and narrow areas, and/ or regions of different thickness.

According to another aspect of the invention, an implant device includes multiple magnetic arrays, and means for preventing attraction between the arrays to facilitate placement of the device in or on a tissue region.

According to another aspect of the invention, a system is provided that comprises a magnetic implant device, and a pocket surgically created in tissue. The pocket is sized and configured with an irregularly shape such that, when the magnetic implant is placed in the pocket, intact tissue around the implant prevents motion of the magnetic implant.

Another aspect of the invention provides a system comprising first, second, and third magnetic structures, each having a north magnetic pole. The first and second magnetic structures are sized and configured for placement in or on a first tissue region in a spaced apart relationship. The magnetic north poles or the first and second magnetic structures are mutually oriented toward a second tissue region. According to this aspect of the invention, the third magnetic structure is sized and configured for placement in or on the second tissue region. The magnetic north pole of the third magnetic structure is oriented toward the first tissue region between the first and second magnetic structures. The offset between the third magnetic structure and the first and second magnetic structures lends stability to the repelling interaction among the magnets in the system.

Another aspect of the invention provides a system for implanting a magnetic implant comprising side-by-side arrays of magnets that can flip or fold upon itself to form a folded-up structure. The system comprises first means for separating the folded-up structure and positioning the magnetic implant in tissue, and second means for holding the magnetic implant in place while the first means separates the folded-up structure.

Another aspect of the invention provides a method for stabilizing a magnetic implant comprising side-by-side first and second magnetic sections. The method threads a placement suture through two adjacent inner holes in the first magnetic section and ties the placement suture to form a loop. The method folds the implant so that the first section overlaps the second section and places the implant while folded through the incision into a pocket formed in wall tissue. The method positions a first instrument to hold the second section against fascia while placing a second instrument through the suture loop. The method pulls the ends of the placement suture to apply force to separate the first and second sections, while using the second instrument to guide the first section into a side-by-side relationship with the second section. The method places anchoring sutures at the four corners of the separated magnetic implant and then cuts the loop to remove the placement suture.

Another aspect of the invention provides methods for inserting a various shaped implants in soft tissue.

One method implants a U-shaped implant. The method cuts two incisions in the soft tissue, and cuts a U-shaped pocket in the soft tissue. The method uses a tool to push suture through one incision into the U-shaped pocket, until one end of the suture comes out through the other incision. The method ties one end of the suture to the U-shaped implant. The method uses a tool to push from one end of the implant, while pulling the suture at the other end of the implant, to fit the U-shaped implant into the specified pocket. The method closes the two incisions.

Another method implants an L-shaped implant. The method cuts an incision in the soft tissue and cuts an L-shaped pocket in the soft tissue. The method uses a tool to push the L-shaped implant into the L-shaped pocket and closes the incision.

Another method implants an O-shaped implant. The method cuts an incision into the soft tissue and cuts an O-shaped pocket into the tissue. The method inserts an O-shaped implant with an open link into the pocket. The method closes the open link of the O-shaped implant in the pocket and closes the incision.

The implant devices, systems, and methodologies that embody technical features of the invention are well suited for placement in structures of the airway, such as the tongue, soft palate/uvula, and pharyngeal wall.

Other inventions and technical features shall be apparent based upon the accompanying description, drawings, and claims.

BRIEF DESCRIPTION OF THE DRAWINGS

FIGS. 8A, 8B, and 8C show various implantable magnetic arrays desirably shaped to provide both stability after implantation, as well as the healing rate post-operatively.

FIGS. 9A, 9B, and 9C show representative embodiments of magnetic implants having at least one side with variegations to provide a tissue gripping surface, thereby providing stability after implantation.

FIGS. 11A(1) to 11A(4); 11B(1) to 11B(5); and 11C(1) to 11C(4) show various representative alternative embodiments of stabilized magnetic implant structures especially adapted for implantation in a posterior pharyngeal wall.

FIGS. 12 and 13 show various types of magnetic implants that include apertures through which external fixation means, e.g., suture or staples, can be passed to attach the implant to surrounding tissue.

FIGS. 14A and 14B show an implant of the type shown in FIG. 8A, which includes a network of holes that can be filled with a growth-stimulating medium to encourage the in-growth of tissue to stabilize the implant.

FIG. 15 shows an implant of the type shown in. FIG. 8A, which includes a network of holes filled a tissue adhesive or glue to give immediate post-op tissue stability.

FIG. 33 shows a magnetic implant having preferential flexibility allowing the implant to remain in position because it closely mimics the movements of the surrounding anatomy.

FIGS. 34A and 34B a magnetic implant having a support brace to help stabilize the implant.

DESCRIPTION OF THE PREFERRED EMBODIMENTS

This Specification discloses various magnetic-based devices, systems, and methods for improved stabilization of magnetic forces both during implantation and at an implanted position. For example, the various aspects of the invention have application in procedures requiring the restriction of tissue collapse in and/or around the body, such as a passageway within the body. The devices, systems, and methods that embody features of the invention are also adaptable for use with devices, systems, and methods that are not restricted to tissue based applications.

The devices, systems, and methods are particularly well suited for treating sleep disordered breathing, including sleep apnea. For this reason, the devices, systems, and methods will be described in this context. Still, it should be appreciated that the disclosed devices, systems, and methods are applicable for use in treating other dysfunctions elsewhere in the body, which are not necessarily sleep disorder related.

I. Magnetic Force Systems

Figure 1:
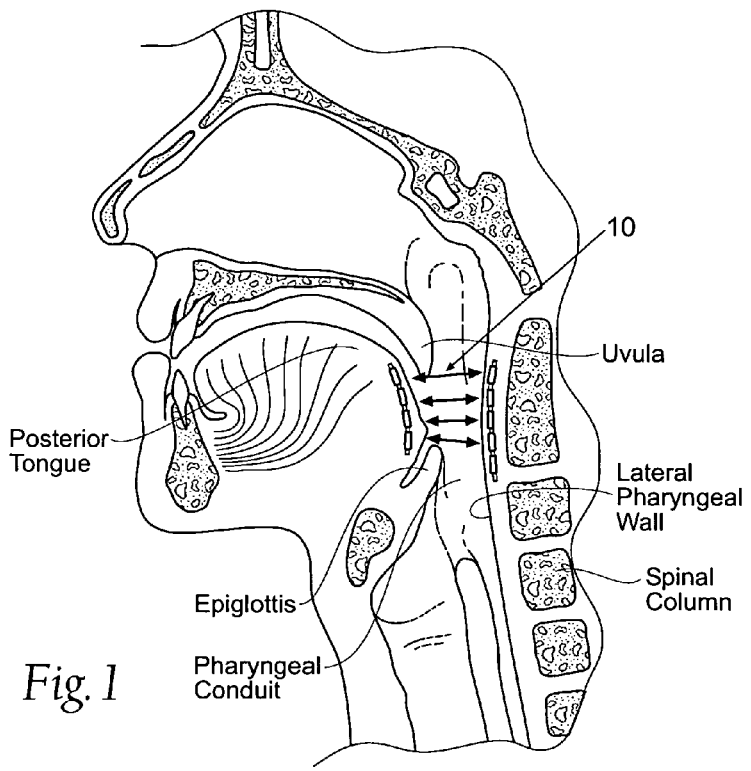
FIG. 1 is an anatomic view of a magnetic force system that includes a first magnetic component implanted in the back of the tongue and a second magnetic component implanted in a posterior region of the pharyngeal wall, the first and second magnetic components having the same polarity to magnetically interact by the generation of a repelling force between them, which prevents the tongue from moving in a posterior direction and closing or restricting the pharyngeal conduit or airway.

FIG. 1 shows, in an anatomic view, an illustrative magnetic force system 10. The magnetic force system 10 resists the collapse of tissue in a targeted passageway, such as a pharyngeal structure and the individual anatomic components within the pharyngeal conduit during sleep. As generally shown in FIG. 1, the magnetic force system includes a first magnetic component 12 implanted in the back of the tongue and a second magnetic component 14 implanted in a posterior region of the pharyngeal wall. The first and second magnetic components 12 and 14 have the same polarity. They magnetically interact by the generation of a repelling force between them. The magnetic repelling force prevents the tongue from moving in a posterior direction and closing or restricting the pharyngeal conduit or airway.

It should be appreciated that the magnetic force system 10 can be differently configured and arranged, both anatomically and with respect to the position and polarity of the magnets.

Figure 2:
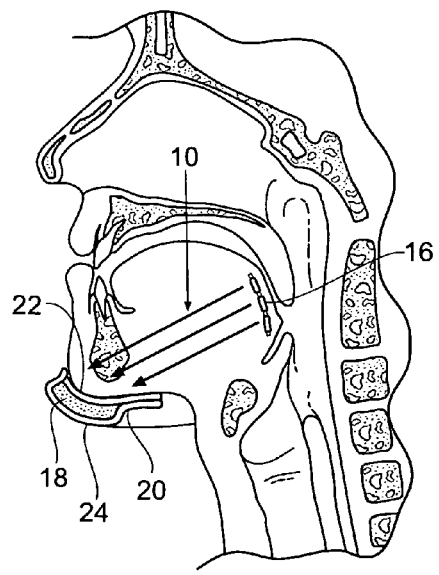
FIG. 2 is an anatomic view of a magnetic force system that includes a magnetic (or ferrous) array implanted near the posterior surface of the tongue and an external magnet that is mounted in a form fitting collar below the mandible and located forward, near the anterior surface of the chin, the magnetic or ferrous array and the external magnet being of opposite polarities to magnetically attract the implanted magnets forward, pulling the tongue in an anterior direction and opening the airway.

For example, FIG. 2 shows a cross section of a human head showing the nasal and oral cavities, tongue, oropharynx, chin and neck. A magnetic (or ferrous or ferromagnetic) array 16 is implanted near the posterior surface of the tongue. An external magnet 18 is mounted in a form fitting collar 20 such that the magnet is positioned below the mandible and located forward, near the anterior surface of the chin. A soft pad 22 provides comfort for the wearer, preventing the magnet 18 from pressing directly against the flesh of the chin. An outer covering 24 encases the magnet and wraps around for the collar 20 to stabilize and anchor the magnet 18 in the desired location. The collar 20 can include a closure means such as a buckle or Velcro® strap for ease of use. The strap may further be elastic to provide a degree of stretch in the collar 20 for head movement, etc. The collar 20 may be comprised of a foam interior with a stretchable fabric covering for softness and breathability.

In use, the magnet 18 has a polarity that is opposite the polarity of the magnetic or ferrous or ferromagnetic array 16. As a result, the magnet 18 will attract the implanted magnets or ferrous or ferromagnetic array 16, pulling the tongue in an anterior direction and opening the airway. This will prevent closure and occlusion of the airway during sleep.

Figure 3:
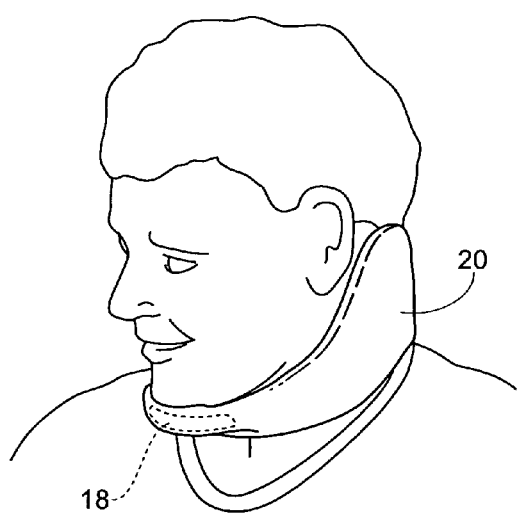
FIGS. 3 to 6 are alternative views of a magnetic force system of the type shown in FIG. 2.

FIG. 3 shows an alternative embodiment of a neck collar 20 with the magnet 18 placed just under the chin.

Figure 4:
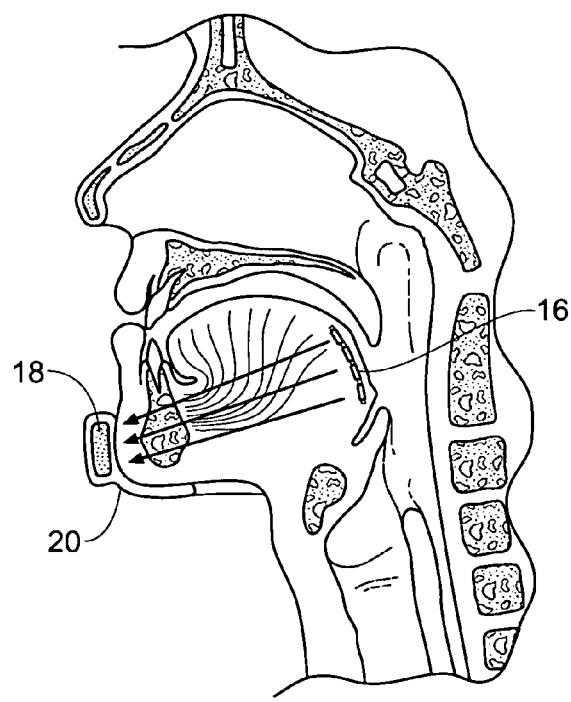

FIG. 4 shows another alternative embodiment. The magnetic or ferrous or ferromagnetic array 16 is implanted near the posterior surface of the tongue. The external magnet 18 of opposite polarity is mounted in a form fitting collar 20 such that the magnet is positioned against the anterior surface of the chin. This arrangement will cause the direction of the attractive force on the implanted array 16 to be directly forward, as opposed to a more-downward direction as in FIG. 2.

Figure 5:
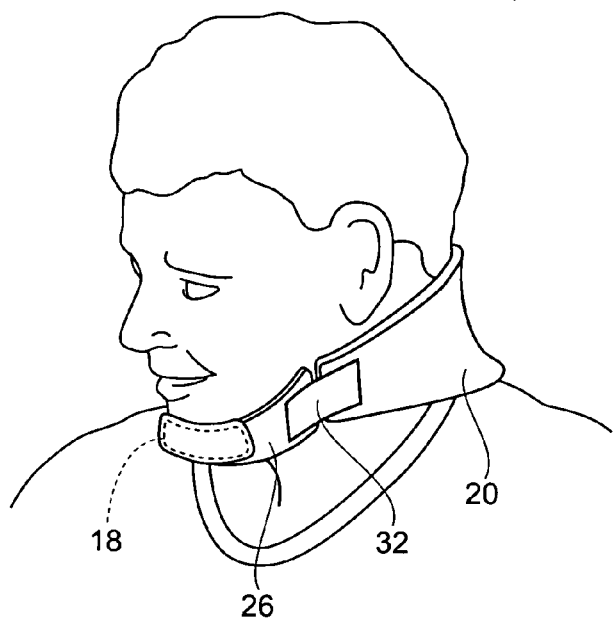

FIG. 5 shows an alternative embodiment, in which the external magnet 18 is held in place by a form fitting appliance 26 and collar 20. Closure and adjustability can be provided by a buckle and strap arrangement or by a Velcro® strap 32.

Figure 6:
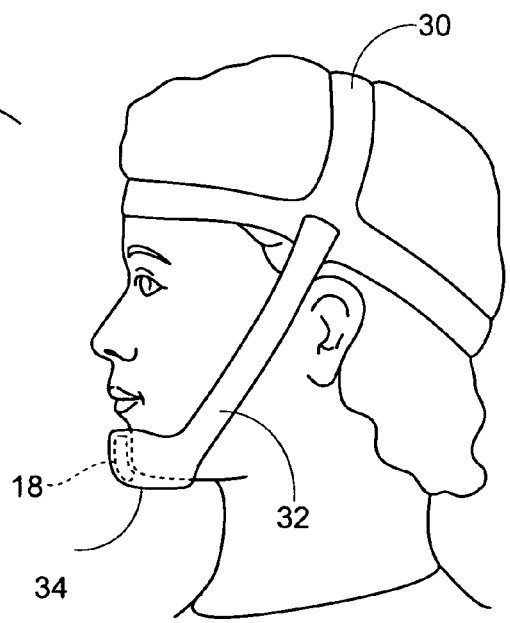

FIG. 6 shows yet another embodiment, in which a headgear 30 is provided consisting of flexible webbing straps. Side straps 32 extend downwardly to cup the magnet and chin cup 34 with the magnet 18 fixed within the chin cup 34. This arrangement has the further advantage of preventing the mouth from falling open during sleep. Open mouth breathing is blamed by some in loud snoring, drying of the mouth and exacerbation of the tendency of the tongue to fall backward into the airway.

Magnetic forces field systems (repelling and/or attracting) can create a magnetic field to resist the collapse of tissue in targeted pharyngeal structures and individual anatomic components within the pharyngeal conduit during sleep. The targeted pharyngeal structures and individual anatomic components within this region can include the pharyngeal walls; the base of the tongue; the vallecula; the hyoid bone and its attachments; the soft palate with uvula; the palatine tonsils with associated pillar tissue; and the epiglottis.

The implanted ferromagnetic material and/or the source of magnetic force can each comprise a single or discrete source of magnetism having a given desired orientation. For example, a single permanent magnet, comprising a body of a ferromagnetic material, can comprise a single source of magnetism having a given orientation.

As another example, a flexible or compliant array of magnets can also comprise individual sources of magnetism carried as a unit on a support carrier, or otherwise directly linked together, as will be described.

II. Magnetic Stabilization.

As previously described, when two or more magnets are placed near each other, a repelling or attracting force will be present and will act upon the two or more magnets.

An attracting force can also be generated between a ferrous alloy/ferromagnetic material and a magnet. The force, when properly directed, provides the benefit of the system 10 in its various embodiments, as described.

The magnetic force can also create difficulty in implanting or positioning the magnets at the targeted tissue region, and can also contribute to the unwanted movement (i.e., migration or extrusion) of the magnets in the tissue region after implantation or positioning. It is desirable to provide magnetic field systems that are stabilized, both during implantation or positioning and after implantation during use.

A. Prevention of Migration and Extrusion After Implantation

1. Offset Repelling Pole Orientation

A repelling magnetic force system is inherently less stable than a counterpart attracting magnetic system. The inherent instability can be mitigated, e.g., by the relative orientation of repelling magnets to provide a preferred repelling position.

Figure 7A:
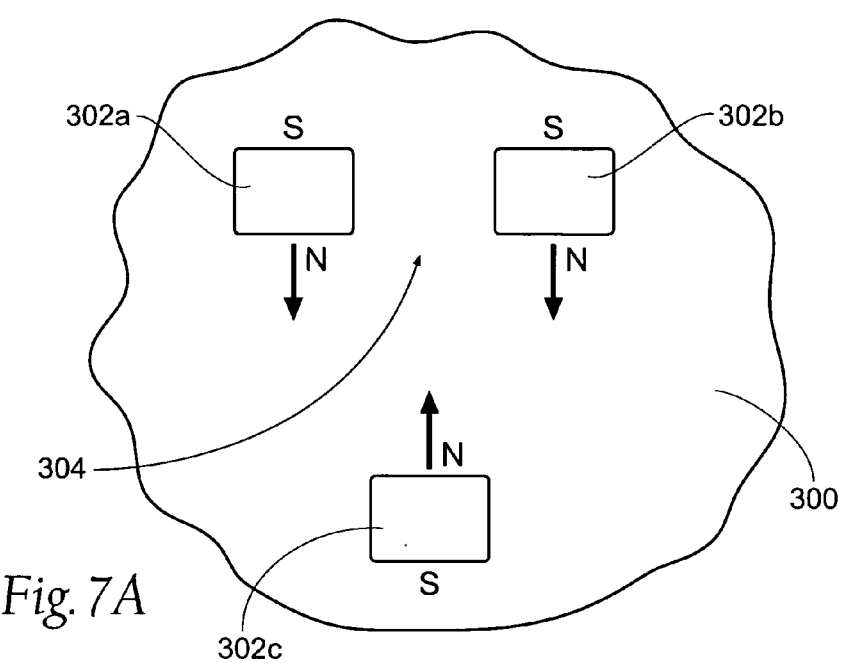
FIG. 7A diagrammatically shows an array of three repelling magnets oriented in a relatively stable repelling position, due to the creation of a magnetic force field saddle shown in FIG. 7B.

For example, FIG. 7A shows an array 300 of three repelling magnets 302a, 302b, and 302c in a relatively stable repelling position. The array 300 orients two magnets 302a and 302b in a laterally spaced-apart relationship, with the magnetic north poles (N) in parallel side-by-side axial alignment. A lateral space 304 separates the magnets 302a and 302b.

Figure 7B:
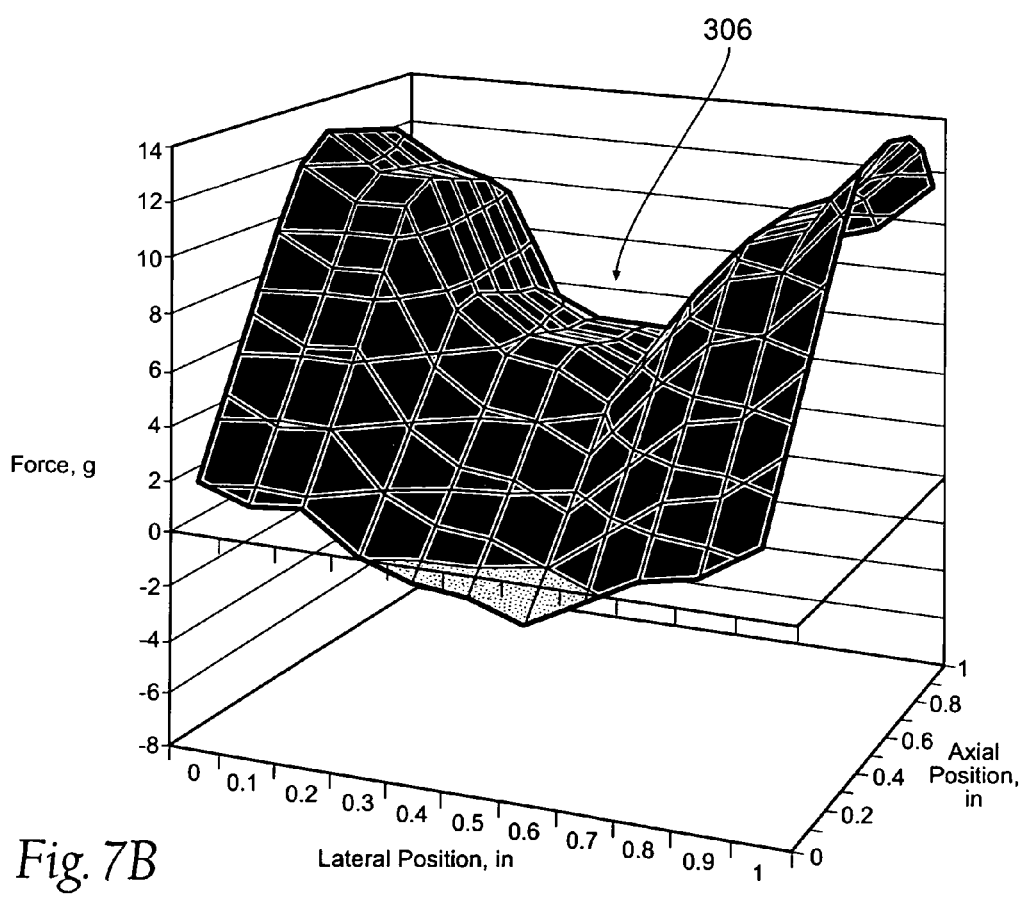

The array 300 places the third magnet 302c in an indirect facing relationship with the two magnets 302a and 302b. As shown in FIG. 7A, the magnetic north pole (N) of the magnet 302c is oriented parallel to the magnetic north poles (N) of the magnets 302a and 302b, but does not directly face the north poles (N) of the magnets 302a and 302b. Instead, the north pole (N) of the magnet 302c is offset and faces the lateral space 304 separating the magnets 302a and 302b. The offset array 300 creates a repelling force saddle 306 (see FIG. 7B) in the magnetic force field, which serves to stabilize or give a preferred repelling position.

2. Shapes that Promote Stabilization

The shape of a magnetic implant's outer edge influences both the stability of an implant in its chosen location, as well as the healing rate post-operatively. FIG. 8A shows an implant 36 comprising flexible or compliant array of magnets 38 arranged in a polymer matrix having an outer profile or shape that is representative of a shape that provides stability in tissue after implantation. As FIG. 8A shows, the magnetic implant 36 has an irregular outer edge 40, with alternating wide and narrow areas. The wide areas prevent motion of the implant as healing occurs around the margins. The capsule that forms around the implant 36 after implantation will contract, grabbing the narrow areas. Holes 43 may be provided to allow tissue in-growth. The rounded corners of the implant 36 allow for faster healing of the surrounding tissues.

FIG. 8B shows an alternate embodiment of a magnetic implant 56 having a profile that is also designed to discourage migration. The implant's flowing curves permit a large area of the surrounding tissues to grow around and grip the implant thus providing a natural anchor. This implant 56 is particularly well suited for implantation in the tongue, which has a naturally curved morphology that matches the profile of the implant 56. The rounded corners 60 and beveled edges 62 further allow for faster healing of the surrounding tissues.

3. Integrated Protrusions for Soft Tissue Fixation

FIG. 8C shows a magnetic implant 36 of a type shown in FIG. 8A having a textured underside 42, or "bottom treads," to grip tissue. Stabilization of the implant 36 (or any implant in general) can also be achieved through attachment of implant parts to the underlying tissue using, e.g., sutures or staples or glue, as will be described in greater detail later. The treads 42 will limit motion relative to the tissue to encourage rapid healing.

FIG. 9A shows a magnetic implant 48 having a posterior, tissue-facing, side that includes variegations 44 to provide a tissue gripping surface. In FIG. 9A, the opposite anterior side 46 of the implant 48 (which typically faces an airway) can also be variegated, but in FIG. 9A the anterior side 46 is shown to be smooth, to aid the epithelial tissue in gliding over the implant during dynamic movement of the surrounding tissue, e.g., during swallowing or speech. In the two-sided arrangement shown in FIG. 9A, the implant 48 provides both stabilizing for the magnetic implant 48 (due to the presence of the variegations 44 on the posterior tissue-facing side), as well as increasing tolerance in patients by avoiding interference with the process of swallowing (due to the relatively un-variegated anterior airway-facing side 46).

Figure 9B:
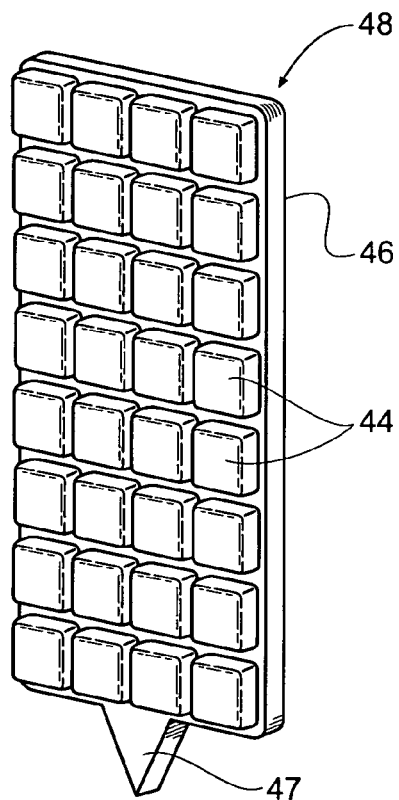
Figure 9C:
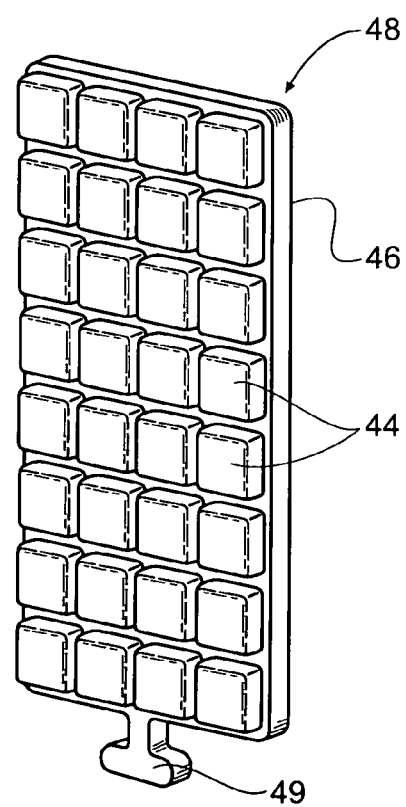

FIGS. 9B and 9C show further embodiments, which are particularly useful for soft tissue fixation in the posterior pharyngeal wall. The posterior pharyngeal wall implants 36 each includes a caudal (inferior)-facing protrusion 47 and 49, shown in FIGS. 9B and 9C, respectively. The caudal-facing protrusions 47 and 49 allow the magnetic implants 36 to become stabilized in a therapeutically-effective caudal-to-cranial orientation (i.e., inferior-to-superior) within the posterior pharyngeal wall, while also avoiding misalignment with respect to the associated magnetic implant or implants in the tongue and/or soft palate/uvula placed to magnetically interact with the pharyngeal wall implants 36.

Treatment of sleep apnea may necessitate insertion of a wide, flat implant in order to generate an effective magnetic field and, at the same time, limit bulking the tissue and making the obstruction worse. In such a case, protrusions such as hooks and barbs are desirably provided to grab the top tissue and limit motion.

Figure 10A:
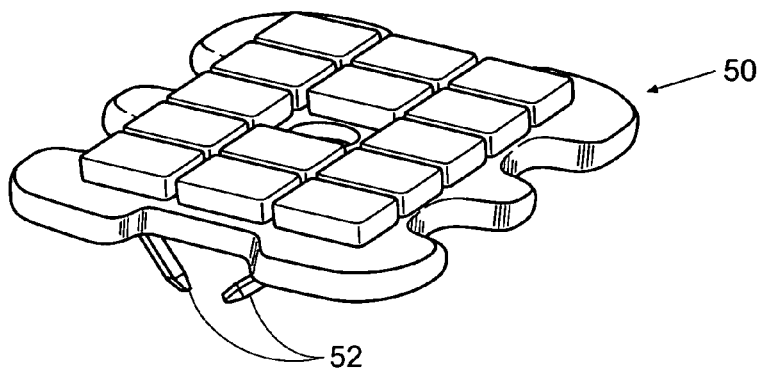
FIGS. 10A, 10B, 10C, and 10D show various types of magnetic implants with hooks, barbs, or a combination of the two, or equivalent components, to prevent migration and folding of the magnetic implant upon itself.
Figure 10B:
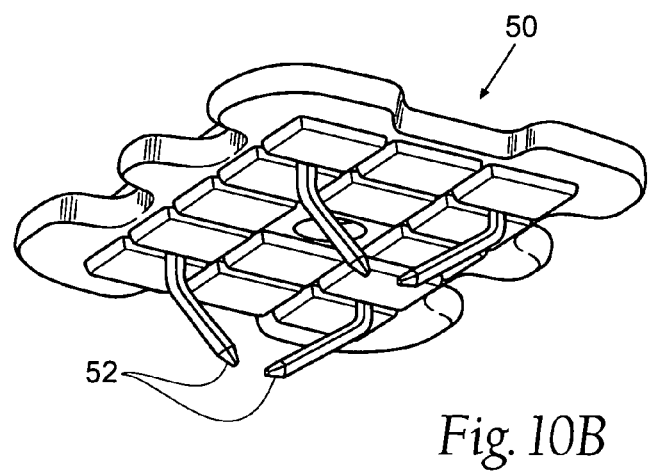
Figure 10C:
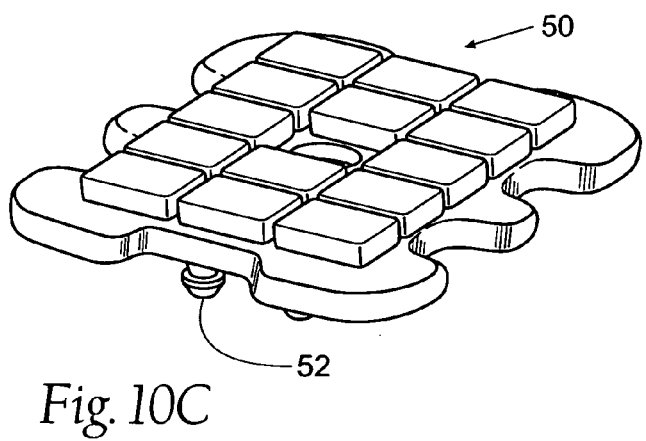
Figure 10D:
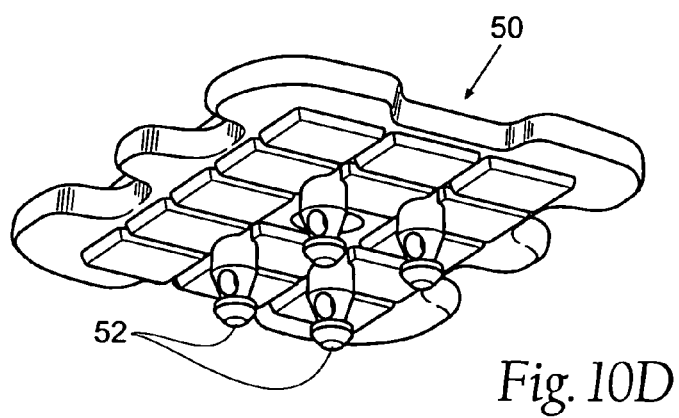

FIGS. 10A and 10B show a representative embodiment of a generally flat implant 50 with hooks 52 that dig into tissue, e.g., in the tongue or oropharynx. FIGS. 10C and 10B show a representative embodiment of a generally flat implant 50 with barbs 52 that provide the same function. The hooks, barbs, or a combination of the two, or equivalent components, prevent migration and folding of the magnetic implant upon itself.

FIGS. 11A(1) to 11A(4) show a representative embodiment of an implant 54 having at least one tissue piercing barb or hook 61, which is especially adapted for implantation in a posterior pharyngeal wall. FIG. 11A(1) shows the implant 54 that includes at least one anchoring assembly 55. Either or both cranial (superior) and/or caudal (inferior) ends of the implant 54 may be straight, gently rounded or curved. The anchoring assembly 55 comprises, at one end, a loop 57 sized and configured for accommodating passage of a tissue suture or staple. In use, the loop 57 is intended to project beyond the cranial edge of the implant 54 for this purpose. The anchoring assembly 55 includes, at the opposite end, a sharp, tissue-piercing or anchoring barb or hook 61. In use, the barb 61 is intended to project beyond the caudal edge of the implant 54. The barb or hook 61 can be manufactured. e.g., from resilient shape memory NiTi wire, resilient formed stainless steel 316L, or any other medical grade metal. The barb or hook 61 can be resiliently straightened by the application of external pressure (as FIG. 11A(2) shows), and will resiliently return toward its curved hook shape in the absence of applied pressure (as FIG. 11A(1) shows).

In the illustrated embodiment (see FIGS. 11A(1) and 11A (2)), the anchoring assembly 55 is sized and configured to be passed, hook end 61 first, through a constricted cranial-caudal channel 63 formed in the implant 54. The channel 63 can be formed, e.g., from NiTi tubing. In use, the channel 63 extends in a cranial-caudal direction, parallel to the longitudinal anatomic axis of the pharyngeal conduit. The channel 63 may extend through holes formed through the individual magnets 65 carried by the implant 54. Alternatively, as shown in FIG. 11A(1), the channel 63 passes through the flexible polymer matrix material of the implant 54 itself.

When introduced into the cranial end of the channel 63 (see FIG. 11A(3)), the hooked end 61 will resiliently straighten within the confines of the channel 63. The hooked end 61 will resiliently return to its hook shape (see FIG. 11A(4)) when freed of the caudal end of the channel 63. It should be appreciated that a given implant 54 can include more than one channel 63 to accommodate a plurality of anchoring assemblies 55, each with a suture loop 57 and a barbed end 61 for fixation of the implant 54 in tissue.

During implantation (see FIG. 11A(3)), the implant device 54 can be placed within a pocket P, e.g., surgically created in tissue in the pharyngeal conduit wall. An X-ray or any other suitable image is desirably taken to ensure that the position of the implant 54 within the tissue pocket P is correct. Once the correct position of the implant 54 in the tissue pocket P is confirmed, the desired number of anchoring assemblies 55 is passed, hook end 61 first, through a channel 63, from cranial end toward the caudal end (see FIG. 11A(3)). Free of the channel 63, the end(s) 61 resiliently return(s) to the hook shape (see FIG. 11A(4)), piercing pharyngeal wall tissue within the pocket P, to anchor the caudal portion of the implant 54 within the pocket P. The cranial end of the implant 54 can then be anchored by suture material S passed through the loop 57 (as FIG. 11A(4) also shows).

Should the implant 54 need to be re-positioned or removed, the suture material S can be removed from the loop 57. By then pulling on the freed loop 57, the hook 61 can be withdrawn from tissue and back into the caudal end of the channel 63 (as FIG. 11A(2) shows). Once the hook 61 is withdrawn and straightened within the channel 63, the implant 54 can be completely removed from the pocket P, or it can be re-positioned and then re-affixed, according to the patient's needs.

FIG. 11B(1) shows another representative embodiment of an implant 54 having at least one tissue piercing barb or hook 67, which is especially adapted for implantation in a posterior pharyngeal wall. In FIG. 11B(1), two hooks 67 are shown. Each barb or hook 67 can be manufactured. e.g., from NiTi wire, stainless steel 316L, or any other medical grade metal. In the embodiment shown in FIG. 11B(1), each barb or hook 67 is permanently affixed to the implant 54, e.g., by coupling to one or two of the magnetic components. The barb or hook 67 extends from the caudal end of the implant 54. A removable protective cover 69 (e.g., made from u-shaped nitinol or any other biocompatible material) is desirably fitted over the barb or hook 67 prior to use (as FIG. 11B(1) shows) and/or during implantation (as shown in FIG. 11B(2)).

During implantation (see FIG. 11B(2)), an implant pocket P is surgically created in the pharyngeal conduit tissue. In this arrangement, the pocket P that is formed is desirably longer than the implant 54 itself, by a distance designated D in FIG. 11(B)(2), e.g., by at least 3 mm. The implant 54 is placed into the pocket P, caudal end first, as FIG. 11B(2) shows. An X-ray or any other suitable image is taken to ensure that the position of the implant 54 is correct. Once the correct position of the implant 54 in the tissue pocket is confirmed, the implant 54 is lowered by a distance less than D (e.g., by approximately 2 mm) into the pocket P, and the protective cover 69 is removed (see FIG. 11B(3)). Each barb or hook 67 pierces pharyngeal wall tissue within the pocket P, to anchor the caudal portion of the implant 54 within the pocket P. The cranial end of the implant 54 can then anchored by suture material S passed through the apertures in the cranial end of the implant 54 (as FIG. 11B(3) shows).

Should the implant 54 need to be removed or re-positioned, the implant pocket P is re-opened, again re-creating a pocket P at least 3 mm longer than the implant 54. The sutures S at the cranial end of the implant 54 are cut and the implant 54 is lowered within the pocket P to release each barb or hook 67 from the surrounding tissue, so that the protective cover 69 can be fitted back over the barbs or hooks 67.

As FIG. 11B(4) shows, a special spatula tool 300 can be used to facilitate of the release of the barbs or hooks 67. The spatula tool 300 has a distal end 302 that is generally the same width as the implant 54. The distal end 302 includes a soft polymer material, sized and configured to engage the sharp ends of the barbs or hooks 67. In use, as FIG. 11B(4) shows, the spatula tool 300 is inserted behind the implant 54 to the implant device 54 to help free the barbs or hooks 67 from the tissue. Once the barbs or hooks 67 of the implant 54 are free of tissue, they will grab the soft polymer material of the distal end 302. The spatula tool 300 and the attached implant 54 can now be readily removed from the pocket P as FIG. 11B(5) shows. Once removed from the pocket P, the barbs or hooks 67 can be disengaged from the distal end 302, and the protective cover 69 can be fitted back over the barbs or hooks 67. The implant 54 is again ready to be re-positioned into the pocket, if desired, in the manner previously described.

The anchoring systems described, with one or more barbs or hooks, allow posterior pharyngeal wall implants to stabilize in desired positions so as to maximize the therapeutic effects of the implant systems.

FIGS. 11C(1) and 11C(2) show another representative embodiment of an implant 54 having at least one tissue piercing barb or hook 71, which is especially adapted for implantation in a posterior pharyngeal wall.

As shown in FIG. 11C(1), the implant 54 includes an anchoring assembly 73 comprising a U-shaped carrier 75, which carries at least one tissue piercing barb or hook 71. In the illustrated embodiment, the carrier. 75 carries a plurality of barbs or hooks 71, As before described, each barb or hook 71 can be manufactured, e.g., from resilient shape memory NiTi wire, resilient formed stainless steel 316L, or any other medical grade metal. The U-shaped carrier 75 slides within tracks 79 formed within the implant 54 between a first position (shown in FIG. 11C(1)) and second position (shown in FIG. 11C(2)). In the first position (FIG. 11C(1)), the barbs or hooks 71 are retracted within the implant 54. In the second position (FIG. 11C(2)), the barbs or hooks 71 extend through holes in the track 79 outward from the implant 54.

During implantation, the implant 54 is placed within a surgically formed tissue pocket P (see FIG. 11C(3)) (e.g., formed in a posterior pharyngeal wall), with the carrier 75 in the first position, retracting the barbs or hooks 71. Once the desired position for the implant 54 is achieved, the carrier 75 is moved to the second position (see FIG. 11C(4)), advancing the barbs or hooks 71 into piercing contact with tissue within the pocket P. One or more sutures S can be applied to the carrier 75 at the cranial end of the implant 54. Should repositioning or removal of the magnetic posterior pharyngeal wall implant 54 be necessary, the carrier 75 can be pulled up to the first position, retracting the barbs or hooks 71, so that the implant 54 re-positioned within or removed from the pocket P.

In an alternative arrangement, the U-shaped carrier 75 need not include side barbs or hooks 71, but comprise an elongated staple that slides within the tracks 79 and exits the caudal end of the implant 54 to engage tissue. In this arrangement, should repositioning or removal of the implant 54 be necessary, the carrier 75 can be pulled up to retract the staple at the caudal end, so that the implant 54 re-positioned within or removed from the pocket P. As before described, one or more sutures can be applied to the carrier 75 at the cranial end of the implant 54.

4. External Fixation Means

Implants need to have features to reduce the stress on the implant, but still allow them to maintain the device shape. Another way to limit stress on a given implant 62 is to include apertures 64 through which external fixation means, e.g., suture or staples, can be passed to attach the implant to surrounding tissue, as illustrated in FIG. 12. This attachment may be to tissue either on the cranial end or the caudal end of the implant. Additionally, if the thickness of the underlying tissue permits, barbs such as silicone extensions (as previously described) may be also incorporated in the implant 62. This design will limit the amount of force applied at the implant edges and prevent motions that can lead to extrusion. Rounded corners 60 are also provided (as previously described) to allow for faster healing of the surrounding tissues.

FIG. 13 shows an implant 66 whose inner edge 68 contains holes 70 to allow the use of surgical thread or suture 72 to anchor the implant to tissue, e.g., into the pharyngeal wall.

5. Tissue In-Growth

The implant 36 shown in FIG. 8A includes a network of holes or cutouts 43 that allow tissue in-growth. The in-growth of surrounding tissue that the holes or cutouts 43 allow further stabilizes the implant. The implant 36 shown in FIG. 8A can be used, e.g., as a tongue implant, with the predetermined cut-outs 43 strategically positioned to promote tissue in-growth. Promoting tissue in-growth is beneficial in providing a lock-in position that further discourages implant migration.

The curved implant 56 shown in FIG. 8B also incorporates an opening 58 in the center of the implant 56 allow for tissue in-growth, further stabilizing the implant. As before stated, this embodiment is particularly well suited for implantation in the tongue. The implant's flowing curves permit a large area of the surrounding tissues to grow around and grip the implant thus providing a natural anchor.

6. Stimulating Tissue In-Growth

FIGS. 14A and 14B show an implant 36 of the type shown in FIG. 8A, in which the network of holes 43 is filled with a growth-stimulating medium 74, which bridges the gap between the upper and lower tissue layers, encouraging rapid healing. FIG. 14B shows a close-up of the growth media 74 used in the implant. The growth-stimulating substance 74 could be bio-absorbable, or act as a scaffold for cell growth. The tissue in-growth will help stabilize the implant.

7. Bio-Compatible Glue

Figure 15:
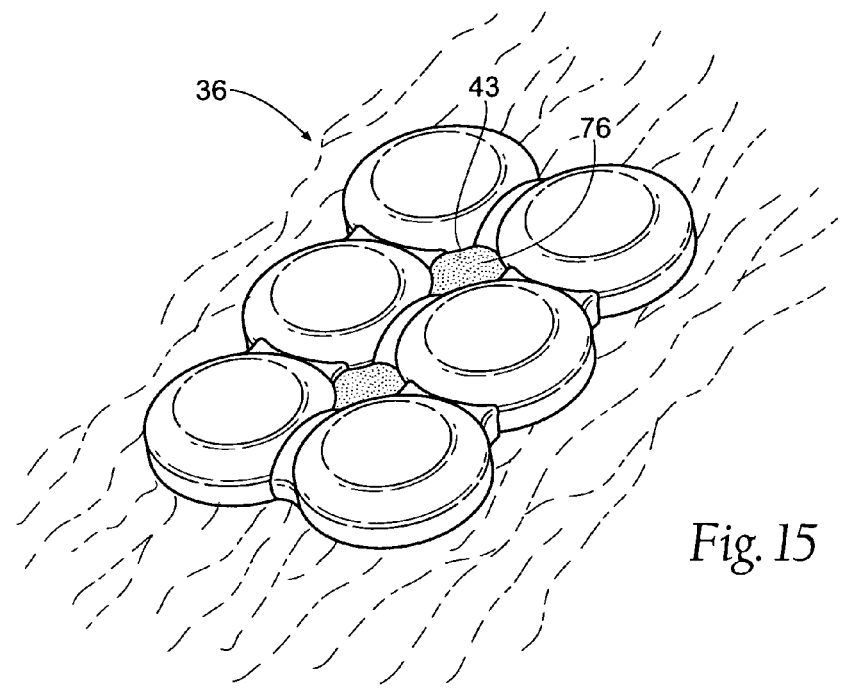

FIG. 15 shows an implant 36 of the type shown in FIG. 8A, in which the network of holes 43 are filled a tissue adhesive 76 or glue (e.g. fibrin glue, cyanoacrylate). Such glue may be used by itself or in conjunction with growth stimulating media 74 (shown in FIGS. 14A and 14B) to give immediate post-op tissue stability.

8. Net Array Implants

Figure 16:
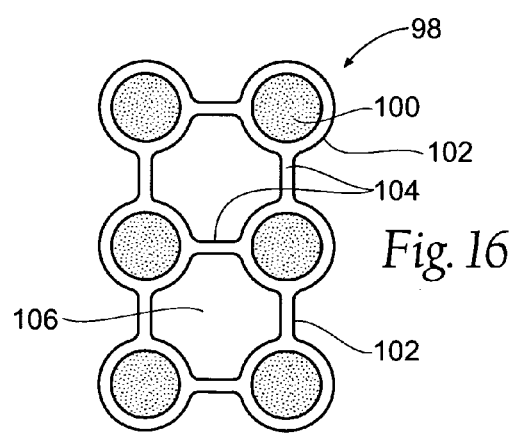
FIGS. 16 to 18 show various types of magnetic net array implants, including magnets or ferrous discs linked together by a net-like webbing with flanges which provide large areas in which the opposing surfaces of the surgically produced pocket may be closed (sutured or otherwise) for fast rejoining and healing of the tissue.

FIG. 16 is a plan view of a net array implant 98. Magnets or ferrous discs 100 are linked together by a net-like webbing with flanges 102 surrounding each of the magnets or ferrous shapes. Each disk 100 is linked to the adjacent disc by a cross web 104, providing protection and isolation from body fluids and tissue.

Figure 17:
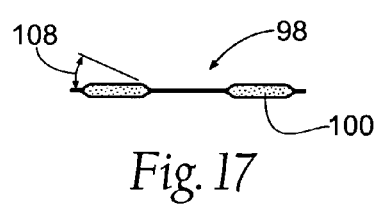

Openings 106 provide large areas in which the opposing surfaces of the surgically produced pocket may be closed (sutured or otherwise) for fast rejoining and healing of the tissue. Further, the narrow flanges surrounding the discs provide clearance for further approximation of the tissue faces. The periphery of the discs (see FIG. 17) is sloped 108 to allow the tissue to form closely around the discs and provide maximum surface tissue contact between the opposing faces of the tissue pocket in which the implant 98 will reside.

The material of which the net array web is produced will preferably be a polymer or compound providing a predictable flexural modulus to allow normal speech and swallowing without discomfort or otherwise affecting these functions. Certain medical grades of silicone rubber, PTFE (polytetrafluoroethylene) Teflon® and certain laminates using Gore Tex® are suitable candidates for this application. An additional and desirable characteristic of the material of which the array web is made will be providing a surface that supports attachment by the surrounding tissue (in-growth). Expanded PTFE and Gore Tex® are known to exhibit this characteristic.

Figure 18:
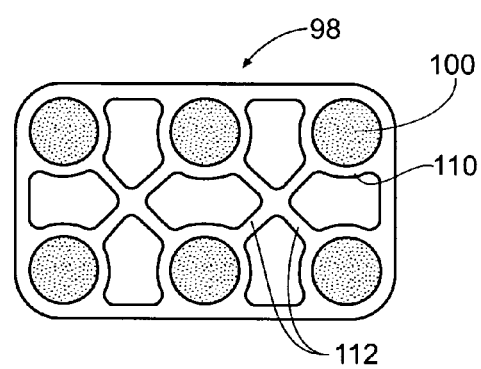

FIG. 18 shows an alternative embodiment of a net array implant 98. In this embodiment, the flanges 110 are linked together around the outside of the array. Also, cross ties 112 diagonally join the discs 100, to provide further stabilization.

Many different configurations of the webbing may be employed to provide varying flexibility or stiffness. For instance, all cross webbing and peripheral links may follow a serpentine path instead of a straight line. This will allow the disks to move toward or away from one another when the muscular tongue tissue lengthens or shortens during speech, swallowing, etc.

Furthermore, the magnetic or ferrous shapes may be other than circular, such as (but not limited to) square, rectangular, oval, elliptical, etc.

The magnetic net array 98 provides a highly stable implanted magnetic or ferrous device, overcoming difficulties related to migration magnet flipping and inadequate forces needed to prevent occlusion of the airway during a sleep related obstructive breathing event. Furthermore, the magnetic net array will allow the healing of the surgical implantation site prior to the application of any attractive or repelling forces and promote speedy healing through close approximation of the wound surfaces.

The net array 98 can be implanted in a stable manner in various ways.

Figure 19:
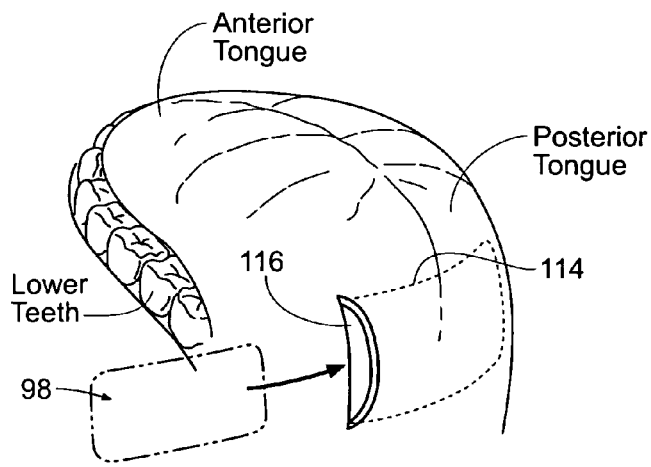
FIGS. 19 to 22 show surgically formed pockets into which magnetic net array implants of the type show in FIGS. 16 to 18 can be implanted for use.
Figure 20:
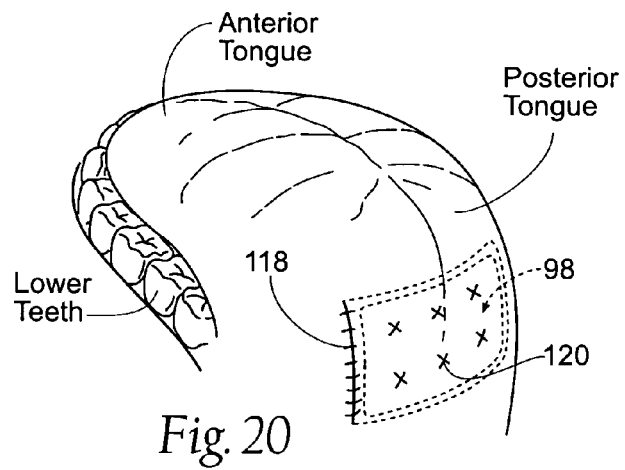

FIG. 19 shows a surgically produced pocket 114 with an opening 116 from the left posterior surface of the tongue. A magnet or ferrous load net array 98 is positioned for placement into the open pocket. FIG. 20 shows the net array 98 inserted and the opening 116 closed using sutures, staples, tissue adhesive or other accepted wound closure means 118. Further suturing 120 or other tissue securing means can be applied in the open areas of the net array 98 to provide tight approximation of the opposing internal surfaces of the pocket. A template may be provided to the surgeon to aid in accurate placement of the sutures in the openings in the array 98.

Figure 21:
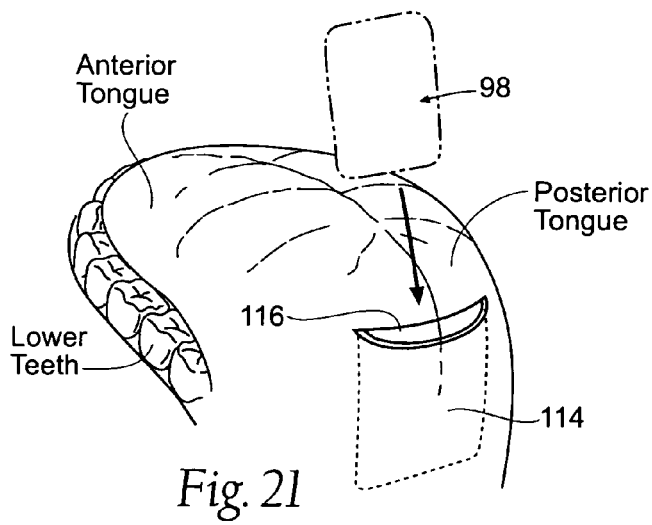
Figure 22:
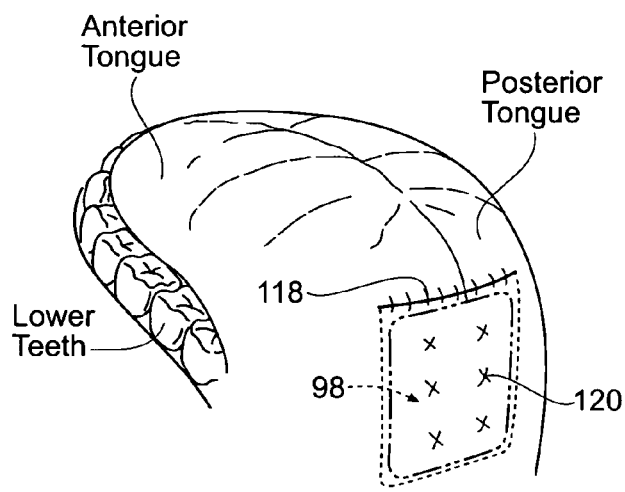

FIG. 21 shows a surgically produced pocket 114 that is oriented vertically instead of the horizontal orientation described above. This approach may be preferred by the surgeon, may be less difficult to perform or may result in improved surgical result. Either approach or other orientation such as angular will be within the intent of the present invention. The opening 116 of the pocket 114 is upward and the net array 98 is positioned into the pocket 114. FIG. 22 shows a net array 98 implanted and the opening closed with suitable closure means 118 as described above. Further, additional sutures or other anchoring means 120 are placed in areas of openings in the net array 98. A template may be provided to the surgeon to aid in accurate placement of the sutures in the openings in the array 98.

9. Specially Dimensioned Surgical Pockets

Figure 23:
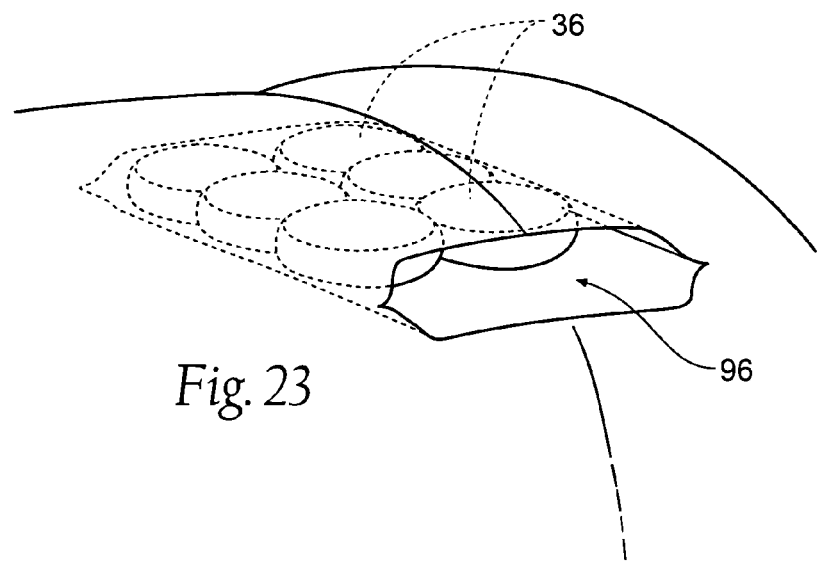
FIG. 23 shows a surgically formed pocket that, with respect to the lateral and longitudinal dimensions of a given implant is laterally-tight but longitudinally-loose to accommodate anterior-posterior movement of the implant, but restrict lateral movement of the implant.

As FIG. 23 shows, a surgically formed pocket 96 may be formed that, with respect to the lateral and longitudinal dimensions of a given implant (for example, implant 36 shown in FIG. 8A), is laterally-tight but longitudinally-loose. FIG. 23 shows, for the purposes of illustration, the implant 36 to be of the type shown in FIG. 8A, but the pocket 96 can be sized to accommodate other types of implants. The pocket dimensions accommodate anterior-posterior movement of the implant 36, but restrict lateral movement of the implant 36. The dimensions of the pocket prevent implant migration, while allowing the implant 36 to move with the tissue, e.g. the tongue, during normal activities.

In addition to the laterally-tight but longitudinally-loose surgical pocket, many different embodiments of surgical pockets are contemplated for "keyed" shapes implants. Such embodiments include, but are not limited to, U-, O-, and L-shaped surgical pockets.

10. Open Implants

Preceding embodiments stabilize various styles of implants by allowing and/or encouraging surrounding tissue to grow through a net-like structure of the magnetic implant's polymer matrix. Another way to stabilize implants is by leaving the tissue in the center of the implant substantially intact.

Figure 24:
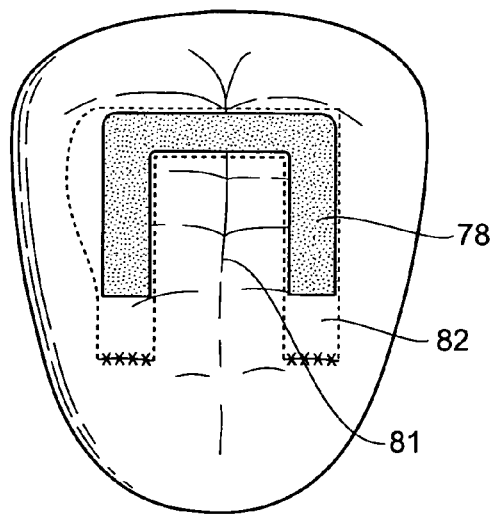
FIG. 24 shows a U-shaped implant placed in a tissue pocket of the same shape (e.g., in a tongue), the implant shape being keyed to prevent migration and limit relative tissue-to-implant motion.

FIG. 24 shows a U-shaped implant 78 placed in a tissue pocket 82 of the same shape (e.g., in a tongue). The tissue 81 in the center of the implant 78 is left substantially intact. Implant shape is keyed to prevent migration and limit relative tissue-to-implant motion.

Figure 25A:
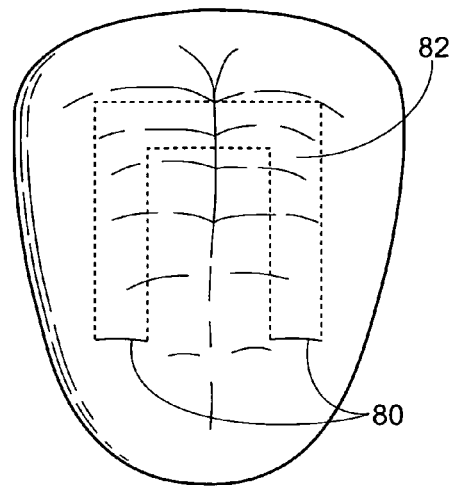
FIGS. 25A to D illustrate a way of inserting a U-shaped implant as shown in FIG. 24 in the tongue.
Figure 25B:
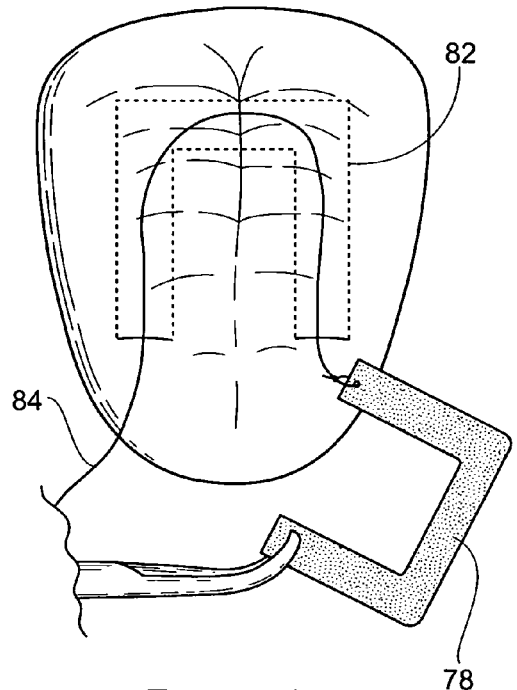
Figure 25C:
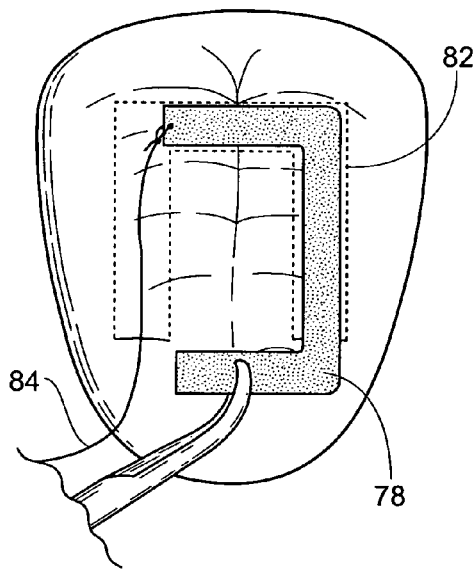
Figure 25D:
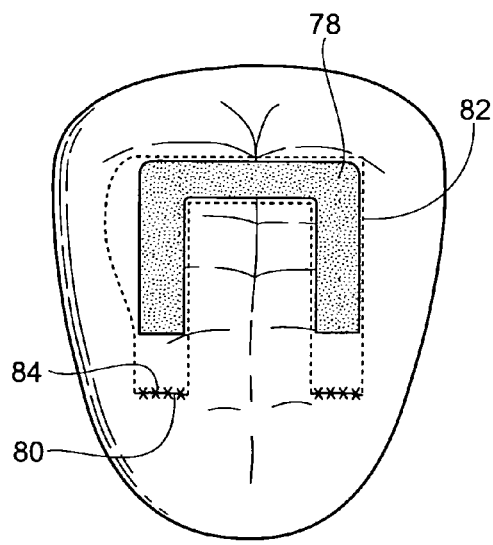

FIGS. 25A to 25D illustrate a way of inserting a U-shaped implant 78 in the tongue. In FIG. 25A two incisions 80 are made in the tongue. The two incisions 80 are used to cut out a U-shaped implant pocket 82 in the tissue. In FIG. 25B, using curved forceps, suture 84 is pushed through the U-shaped pocket 82. One end of the suture is then tied to the implant 78. In FIG. 25C, using curved forceps at one end for pushing the implant and gently pulling the implant from the other end, the U-shaped implant 78 is fitted into the pocket 82. During this process, one leg of the U-shaped pocket becomes enlarged as the implant turns in the pocket. In FIG. 25D, the two incisions 80 are closed up with stitches 84. This method allows the implant to effectively stabilize in its specified location.

Figure 26A:
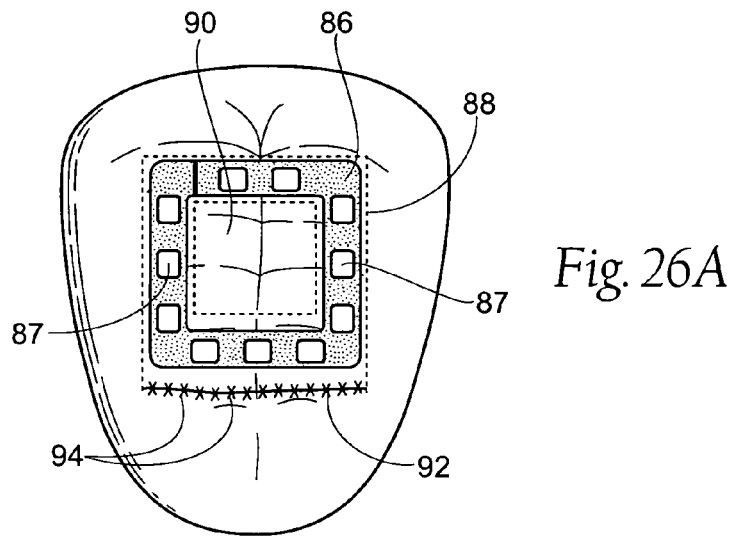
FIG. 26A shows an O-shaped implant placed in a tissue pocket of the same shape (e.g., in a tongue), the implant shape being keyed to prevent migration and limit relative tissue-to-implant motion.

FIG. 26A shows an O-shaped implant 86 placed in a tissue pocket 88 of the same shape (e.g., in a tongue). As with the U-shaped implant 78, the O-shaped implant 86 leaves tissue 90 in the center of the implant 86 substantially intact. This implant shape is also keyed to prevent migration and limit relative tissue-to-implant motion.

Figure 26B:
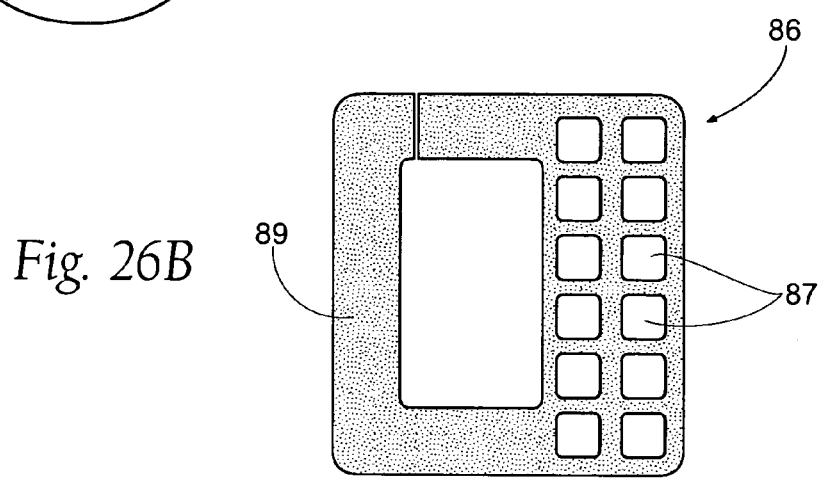
FIGS. 26B and 26C show an O-shaped implant of the type shown in FIG. 26A where magnets are positioned on only one side, the side without magnets acts as a rudder to distribute the force of the tongue and to stabilize the implant.
Figure 26C:
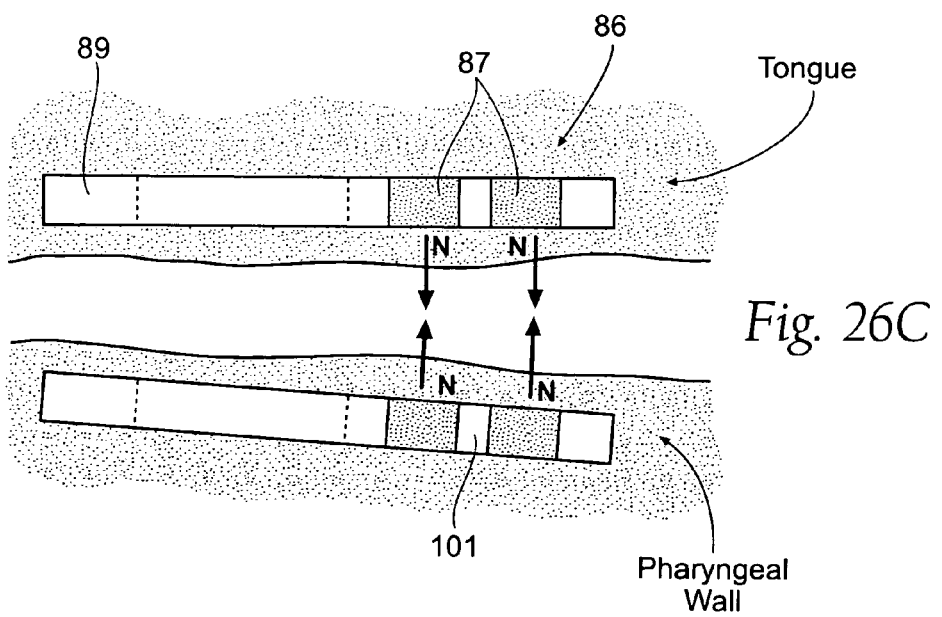

FIG. 26B shows an O-shaped implant 86 where magnets 87 are positioned on only one side. The side 89 without magnets acts as a rudder to distribute the force of the tongue and to stabilize the implant. The opening in center incorporates intact tongue raphe tissue to resist de-centering. FIG. 26C shows a side view of the interaction between the one-sided O-shaped implant 86 of the type shown in FIG. 26B and a corresponding repelling pharyngeal wall implant 101.

Figure 27A:
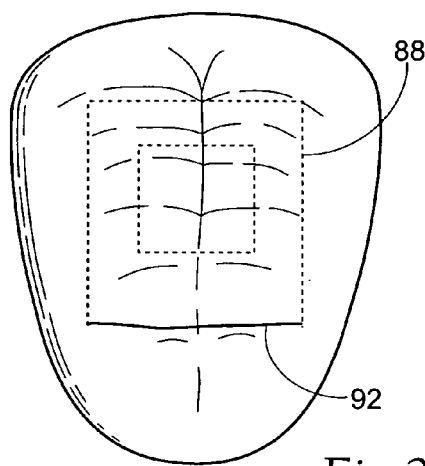
FIGS. 27A to 27D illustrate a way of inserting an O-shaped implant, as shown in FIGS. 26A or 26B, in a tongue.
Figure 27B:
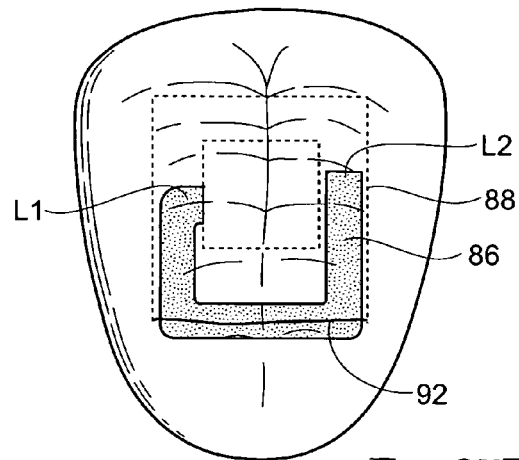
Figure 27C:
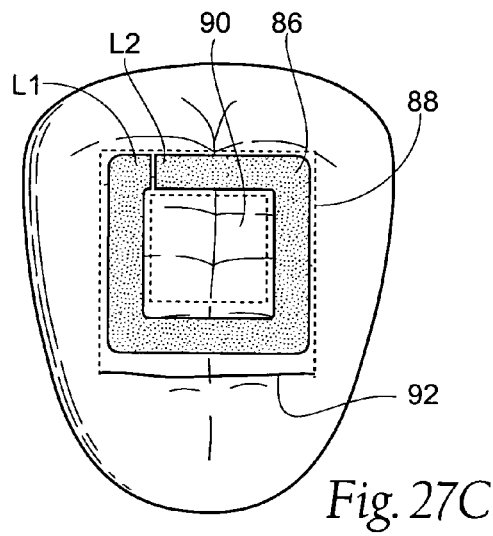
Figure 27D:
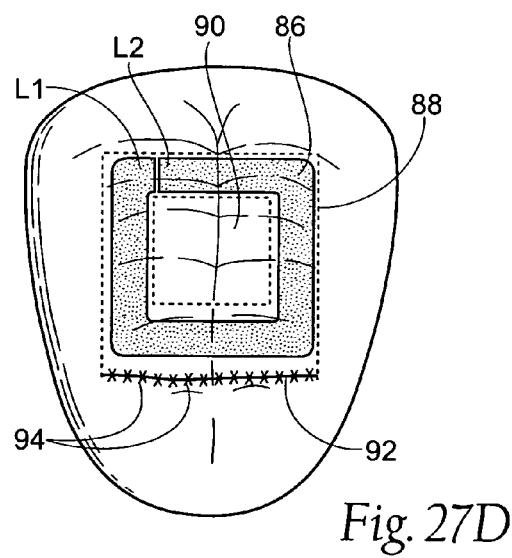

FIGS. 27A to 27D illustrate a way of inserting an O-shaped implant 86, as described. The O-shaped implant 86 may have magnets 87 on both sides, as for example the embodiment shown in FIG. 26A, or only on one side, as for example the embodiment shown in FIG. 26B. Both types of O-shaped implants would use the same insertion method. In FIG. 27A, an incision 92 is cut in the tongue and the O-shaped pocket 88 is created in the tissue. In FIG. 27B, the O-shaped implant 86 with open links L1 and L2, i.e., in an open configuration, is inserted into the O-shaped pocket 88. In FIG. 27C, the open link L2 of the O-shaped implant 86 is inserted around a posterior corner of the O-shaped pocket 88, drawing the other open link L1 to the opposite posterior corner. The links L1 and L2 adjoin (as FIG. 27C shows), thus changing the implant 86 to a closed configuration. In FIG. 27D, the incision 92 is closed up with stitches 94. With this method as well, the implant is firmly stabilized in its specified location.

B. Prevention of Implant Folding or "Flipping" During and After Implantation Arrays of side-by-side magnets can attract each other during implantation and (if not suitably stabilized) after implantation, causing the implant to fold or flip inward upon itself.

Such implant assemblies can be stabilized by providing more rigid cross-support structures between the arrays to prevent the motion of attracting the two arrays together. FIG. 13, previously described, shows an implant 66 with stiff sections 122 between the two magnetic arrays 124 and 126. The stiff section 122 prevents migration of the two sections 124 and 126 of the implant toward one another via attraction during implantation.

Figure 28:
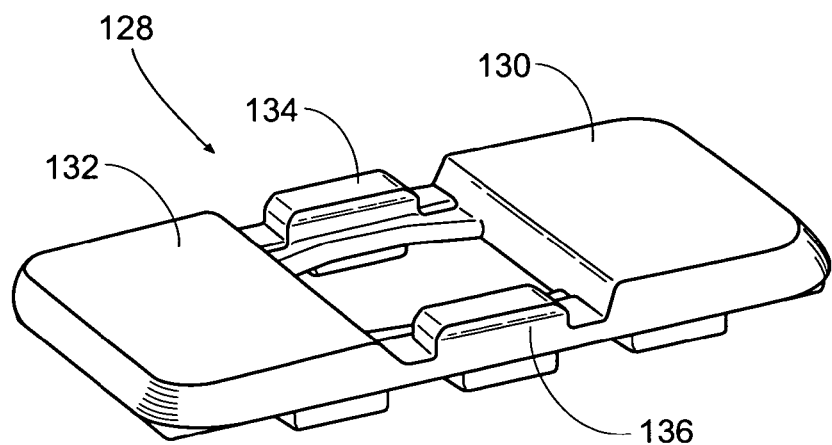
FIGS. 28 and 29 show magnetic implants having a structure that prevents folding during implantation.

FIG. 28 shows an alternative embodiment of a magnetic implant 128 having a structure that prevents folding during implantation. The magnetic implant 128 consists of two main magnetic sections 130 and 132, flexibly joined together by two smaller rigid structures 134 and 136. The flexible juxtaposition of the two smaller rigid structures 134 and 136 provides four potential twisting points through which the implant 128 may flexibly twist, but the implant 128 will avoid folding.

Figure 29:
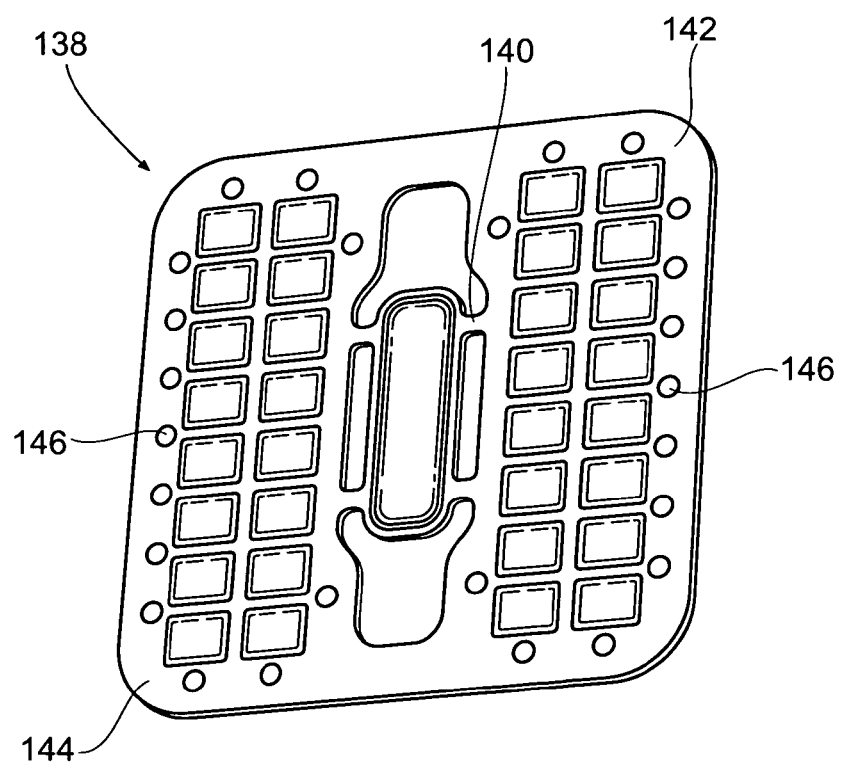

FIG. 29 shows an alternative embodiment of a magnetic implant 138 which includes middle webbing 140 integrated between two magnetic sections 142 and 144 into the magnetic implant device to keep the implant 138 from folding upon itself during implantation. The middle webbing 140 contains a rigid structure for increased rigidity during the insertion process. Once the implant 138 is in a desired (and stabilized) position (e.g., by suturing through the holes 146 provided), the middle webbing 140 may be cut and removed. The implant 138 is thereby rendered flexible after implantation, while resisting folding during implantation.

Figure 30A:
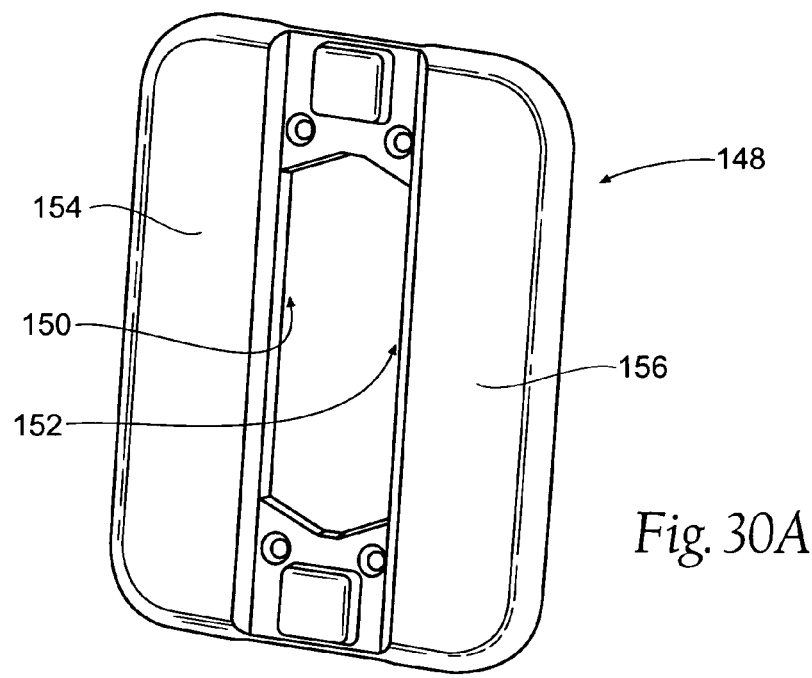
FIGS. 30A to 30C show a magnetic implant which includes flexible hinges between arrays of magnetic discs, which allow the arrays to pivot into a serpentine shape (see FIG. 30C), but prevent the arrays from folding upon themselves.
Figure 30B:
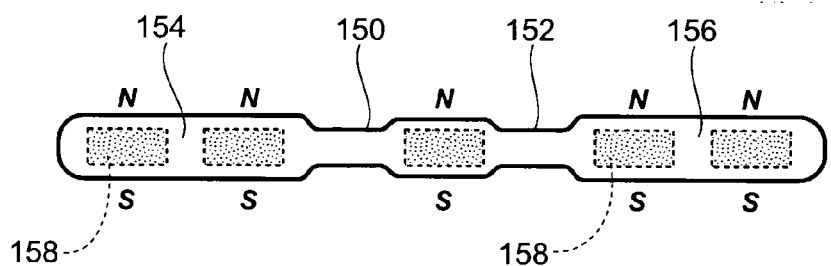
Figure 30C:
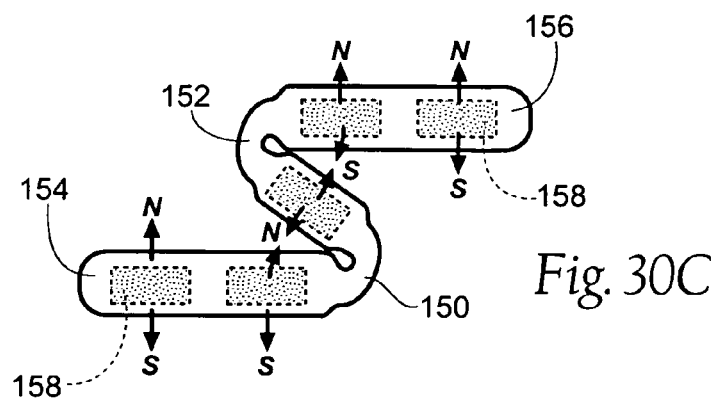
Figure 31:
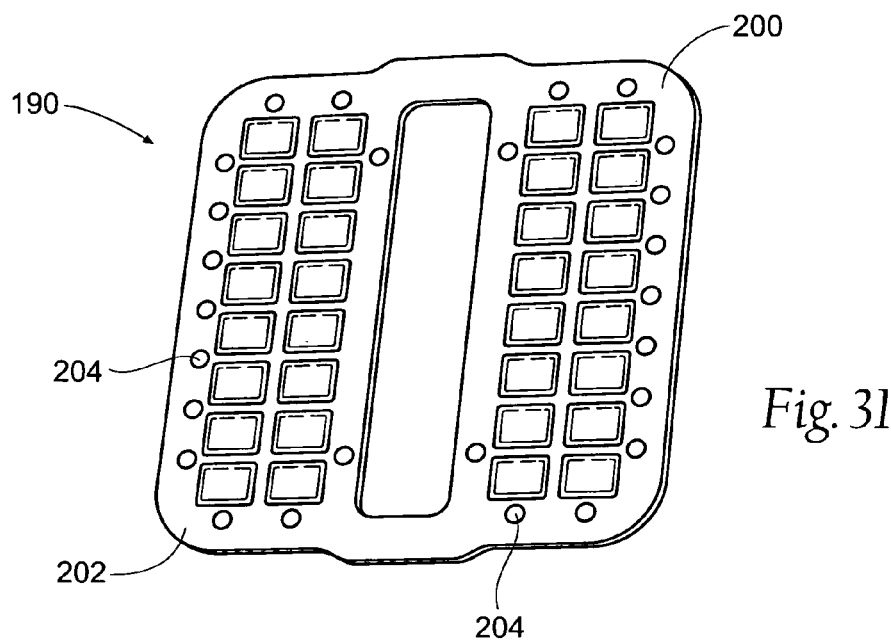
FIG. 31 shows a magnetic implant (shown prior to implantation) having magnetic arrays that are prone to folding or flipping upon itself in response to magnetic interaction.

FIGS. 30A to 30C show an alternative embodiment of a magnetic implant 148 which includes flexible hinges 150 and 152 between two arrays 154 and 156 of magnetic discs 158. FIGS. 30B and 30C show the north (N)-south (S) polarity of the magnetic discs 158. The flexible hinges 150 and 152 allow the arrays 154 and 156 to pivot into a serpentine shape (see FIG. 30C), but prevent the arrays 154 and 156 from folding upon themselves.

Some of the implant assemblies described above are stiffened by the presence of rigid cross-support structures between the magnetic arrays to prevent the attracting forces between the arrays from flipping or folding the arrays upon themselves. However, it may be desirable for certain implants to have a desired degree of flexibility, even if they are thereby made prone to flipping. For these implants, it is desirable, during implantation, to control the separation of the magnetic arrays until fixation and stabilization of the implant at the implant site can be accomplished, e.g., by suturing or other forms of fixation.

Figure 32A:
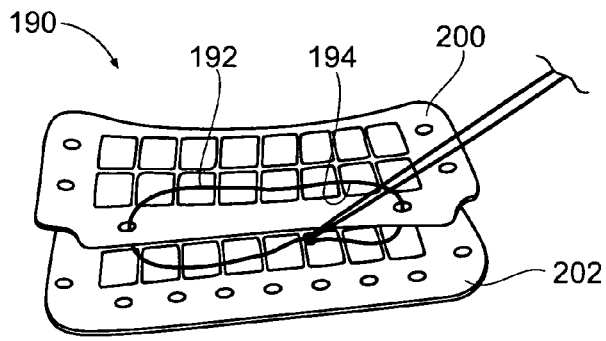
FIGS. 32A to 32D show tools and related methodology for controlling the separation of the magnetic arrays of the magnetic implant shown in FIG. 31, to prevent folding or flipping during implantation.

FIGS. 31 and 32A to 32D show tools and related methodology for controlling the separation of the magnetic arrays 200 and 202 of a magnetic implant 190 (shown prior to implantation in FIG. 31) that is prone to folding or flipping upon itself in response to magnetic interaction. As FIG. 32A shows, suture 192 is threaded through one of the magnetic arrays 200 of the implant 190 and tied to form a loop 194. As FIG. 32A also shows, after the suture loop 194 is formed, the implant 190 is folded so that the magnetic arrays 200 and 202 overlap. Folded over, the implant 190 is placed through an incision into a tissue pocket (e.g., like the pockets shown in FIGS. 19, 21, or 23).

Figure 32B:
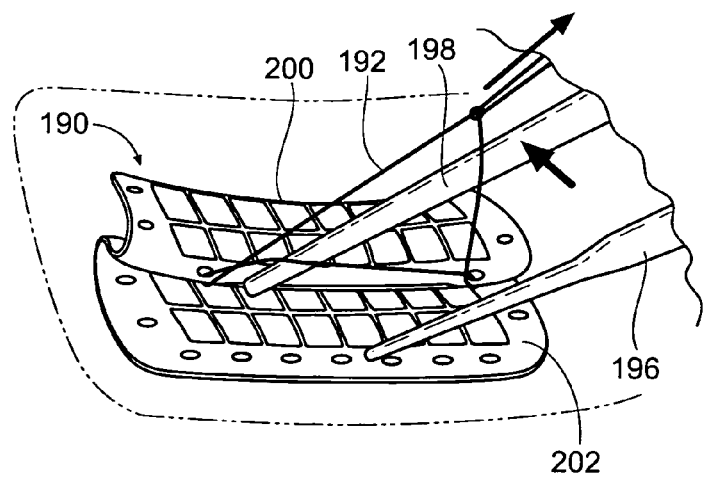
Figure 32C:
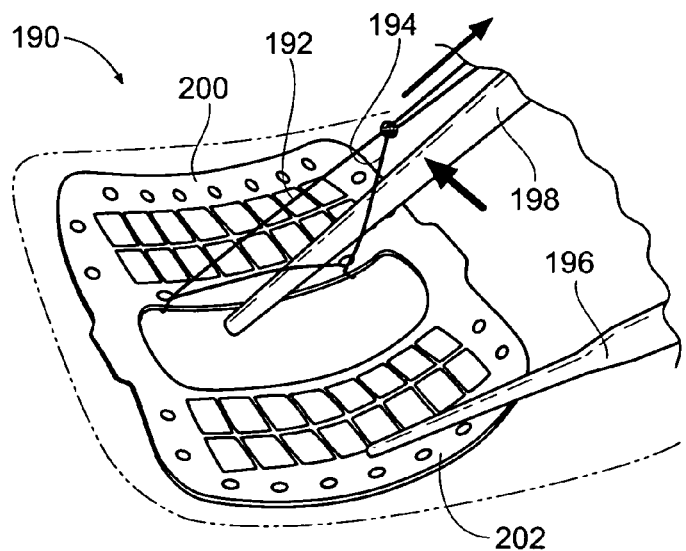
Figure 32D:
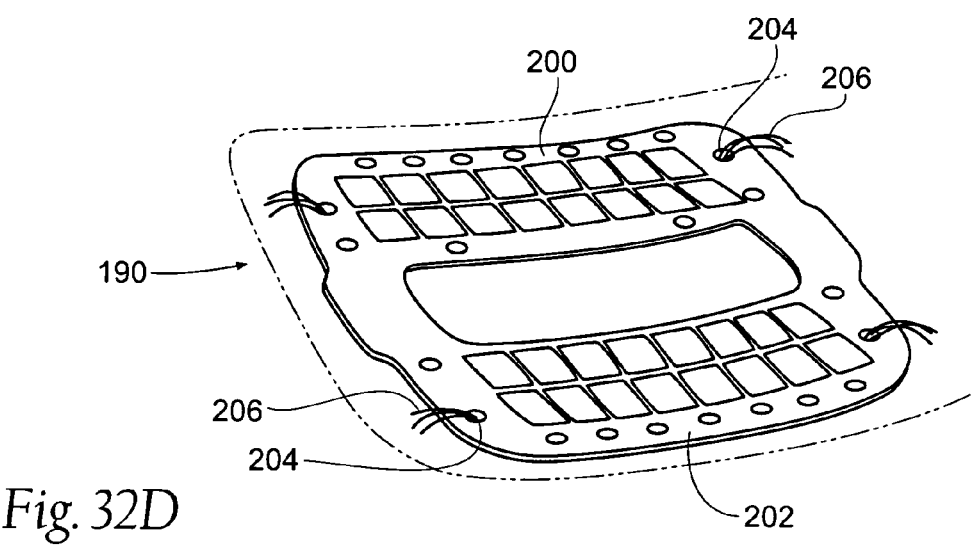

As FIG. 32B shows, within the pocket, a first non-magnetic surgical instrument 196 holds the magnetic array 202 of the implant 190 against the tissue fascia. A second non-magnetic surgical instrument 198 is placed through the suture loop 194. As FIGS. 32B and 32C show, the suture loop 194 is pulled as the first instrument 196 holds the magnetic array 202 against tissue, and as the second instrument 198 pulls the ends of the suture 192 up and slightly to the side to separate the magnetic array 200 from the magnetic array 202. As the loop 194 is pulled, the second instrument 198 continues to guide the magnetic array 200 to separate the magnetic arrays 200 and 202 within the pocket. As FIG. 32D shows, with the magnetic arrays 200 and 202 separated, suitable anchoring sutures 206 are threaded through suture holes 204 provided in the arrays 200 and 202 to secure each magnetic array 200 and 202 to tissue within the pocket. The placement suture 192 is then cut and removed. The instruments 196 and 198 are withdrawn and the pocket closed.

The instruments 196 and 198 that can be used for separating magnetic arrays include: forceps, compass-like spreaders, forceps, tongue-blades and needle-holders. They are manufactured out of non-magnetic materials, e.g., titanium.

C. Other Technical Features

1. Implants for the Pharyngeal Wall

The pharyngeal wall is a dynamic structure that undergoes considerable movement on a daily basis. For a pharyngeal wall implant to be well tolerated, such an implant must be able to be stabilized effectively, while remaining flexible in a posterior-anterior direction.

FIG. 33 shows an implant 158 having spanning members 160 between the magnetic array sections 162, extending along the vertical (elongated) axis on both sides of the centerline. The spanning members 160 each have a reduced thickness, compared to the thickness of the magnetic array sections 162. The thinner cross section of the spanning members 160 facilitates flexibility in the anterior-posterior direction, while the thicker magnetic array sections 162 discourage flexibility in the medial-lateral direction. This preferential flexibility allows the implant to remain in position because it closely mimics the movements of the surrounding anatomy.

The implant 158 has other features described above to impart stability and comfort while implanted, e.g., holes for accommodating passage of sutures or fasteners for fixation, and rounded corner edges and beveled side edges 166 to promote faster healing.

Posterior pharyngeal wall implants present special challenges due to the difficulty associated with the attachment/suturing of the caudal end of the implants to the tissue in the posterior wall. Rectangular posterior pharyngeal wall implants are often susceptible to misalignment with relation to the spine. A misalignment with respect to the spine will offset the magnetic interaction between the tongue/soft palate/uvula implant and the posterior pharyngeal wall implant. If the rectangular device is attached only on top part using sutures, then the magnetic force from the tongue base will swing laterally and misalign the back-wall plate.

FIGS. 34A and 34B show a way to help stabilize the posterior pharyngeal wall implant 54 into a position that, while not hindering the natural movement of the posterior wall, provides enough stiffness to the posterior pharyngeal wall implant to prevent the pendulum-like motion. In other words, the implant 54 allows for posterior-anterior motion for the normal functioning of the posterior pharyngeal wall, while preventing lateral motion that would cause the tissue pocket to tear or re-open.

As shown in FIGS. 34A and 34B, the implant 54 includes a support brace 180 secured to the posterior (tissue facing) side of the implant 54. The support brace 180 is thin and combines the shape of a cross and the shape of a trident. The support brace 180 includes a vertical axis 181, with a hole 183 on each of the caudal and cranial ends for suturing the cranial and caudal ends of the implant 54. The support brace 180 includes a horizontal component 185 with two handles 187 raised at an angle between 90° and 180° from each end. Each of the handles 187 contains a hole 189 for suturing the support brace 180 to the posterior pharyngeal wall tissue.

The posterior pharyngeal wall implant support is desirably made of a material that is elastic in its posterior-anterior movement while rigid with regard to lateral movement and twisting about the vertical axis of the support. Such materials include titanium, biocompatible plastics, as well as other biocompatible materials.

Figure 35:
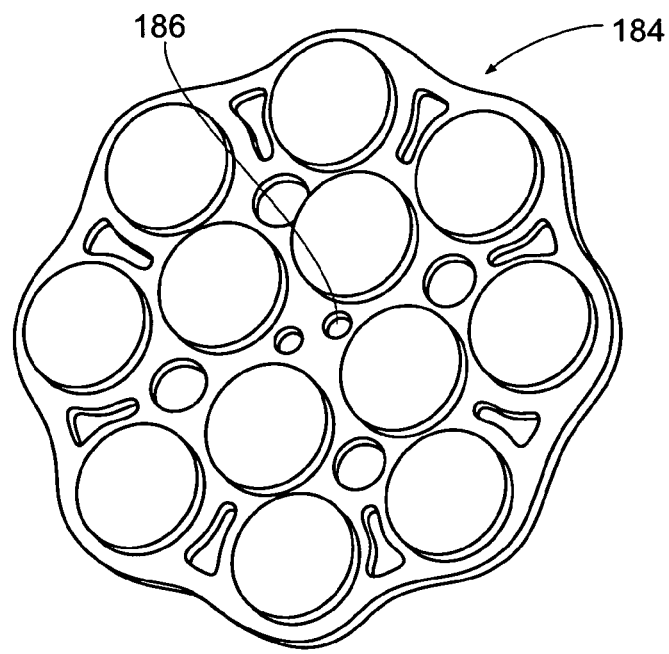
FIG. 35 shows an alternative, circular design for the magnetic posterior pharyngeal wall implant.

FIG. 35 shows an alternative design for the magnetic posterior pharyngeal wall implant. The posterior pharyngeal wall implant 184 is circular, with the attachment holes 186 placed in the center. The circular design is sutured into place over the spine at the center of the circle.

Assuming that the tongue implant is collinear with the spine, then the circular magnetic pharyngeal wall implant is attached at its center over the spine. The circular shape favors perfect alignment without any additional anchoring or correction. If the circular shape is attached at the center, then it has a self-centered geometry, as seen in FIG. 35.

2. Implants for the Tongue

Figure 36:
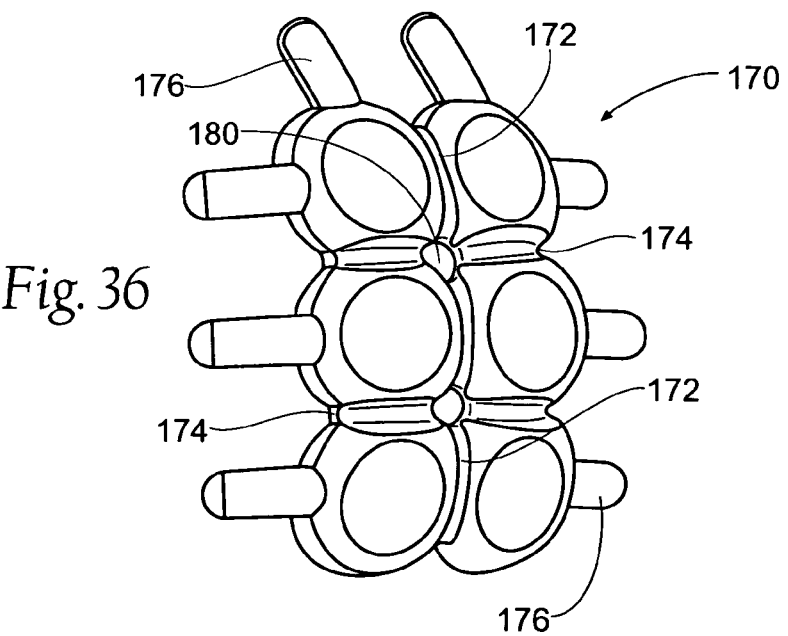
FIG. 36 shows a magnetic implant having preferential flexibility that takes into account the shape and movement of the tongue.

FIG. 36 shows an implant 170 adapted for implantation in a tongue. The implant 170 provides preferential flexibility that takes into account the shape and movement of the tongue. The implant 170 includes flexible cross members 172 that extend along the long (longitudinal) axis that are thicker than (and thus less flexible than) the cross members 174 that extend along the short (transverse) axis. The design of this implant 170 promotes longitudinal stiffening and discourages the implant from folding in on itself. The thinner cross members 174 running across the narrower areas of the implant 170 allow for flexibility which closely mimics the movements of the tongue during normal oral activities. This embodiment of the invention has the advantage of combining implant stability with increased tolerance in the patient.

The implant 170 has other features described above to impart stability and comfort while implanted. For example, the implant 170 also includes integrated fixation tabs 176 that extend outward from the magnetic discs 178 to engage adjacent tissue and provide enhanced fixation and stabilization. The implant also includes holes 180 for tissue in-growth or the placement of a tissue in-growth promoting material or bio-adhesive, as previously described.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the technical features of the invention.

We claim:

1. An implant device comprising:
   at least two ferromagnetic components;
   a support structure having a surface configured to carry the at least two ferromagnetic components in a spaced apart relationship;
   at least one opening formed in the support structure between the at least two ferromagnetic components; and
   at least one protrusion which extends from the support structure in a plane which is parallel to the surface of the support structure, and is sized and configured for engaging tissue to stabilize the support structure.

2. The implant device of claim 1, wherein the at least one opening is sized and configured to accommodate tissue in-growth.

3. The implant device of claim 2, further including a tissue growth stimulating substance carried in the at least one opening.

4. The implant device of claim 1, further including a biocompatible glue carried in the at least one opening.

5. The implant device of claim 1, wherein the at least one opening is sized and configured to accommodate placement of an external fixation element.

6. The implant device of claim 5, wherein the external fixation element comprises a suture.

7. The implant device of claim 5, wherein the external fixation element comprises a staple.

8. The implant device of claim 1, wherein the support structure comprises a polymer matrix.

9. The implant device of claim 1, wherein the support structure allows flexure between the at least two ferromagnetic components.

10. The implant device of claim 1, wherein the support structure comprises a net-like array of openings.

11. The implant device of claim 1, wherein the opening occupies a geometric center of the support structure.

12. The implant device of claim 11, wherein the support structure is generally U-shaped, or L-shaped, or O-shaped.

13. The implant device of claim 11, wherein the support structure is generally circular.

14. The implant device of claim 13, wherein the support structure includes links that adjoin to form a generally circular shape.

15. The implant device of claim 1, wherein the support structure is stiffened adjacent the at least one opening.

16. The implant device of claim 1, wherein the support structure includes a first side having a textured surface sized and configured for contact with tissue and a second side having a generally smooth surface.

17. The implant device of claim 1, wherein the support structure includes rounded corners.

18. The implant device of claim 1, wherein the support structure includes irregular outer edges forming alternating wide and narrow areas.

19. The implant device of claim 1, wherein the support structure includes regions of different thickness.

* * * * *